US007178386B1

(12) United States Patent
Gamble et al.

(10) Patent No.: US 7,178,386 B1
(45) Date of Patent: Feb. 20, 2007

(54) PARALLEL FLUID PROCESSING SYSTEMS AND METHODS

(75) Inventors: Ronald C. Gamble, Altadena, CA (US); Sergey I. Osechinskiy, Arcadia, CA (US)

(73) Assignee: Nanostream, Inc., Pasadena, CA (US)

( * ) Notice: Subject to any disclaimer, the term of this patent is extended or adjusted under 35 U.S.C. 154(b) by 79 days.

(21) Appl. No.: 10/821,567

(22) Filed: Apr. 9, 2004

Related U.S. Application Data

(60) Provisional application No. 60/461,846, filed on Apr. 10, 2003.

(51) Int. Cl.
*G01N 30/02* (2006.01)
*B01D 15/08* (2006.01)

(52) U.S. Cl. ............... 73/61.57; 73/1.01; 73/61.52; 210/198.2

(58) Field of Classification Search ............... 73/1.01, 73/61.52, 61.55, 61.56, 61.57, 61.58; 210/198.2
See application file for complete search history.

(56) References Cited

U.S. PATENT DOCUMENTS

| | | | |
|---|---|---|---|
| 3,733,474 A | | 5/1973 | Edwards et al. |
| 3,827,302 A | | 8/1974 | Sato |
| 3,845,288 A | | 10/1974 | Cornyn, Jr. et al. |
| 4,141,237 A | | 2/1979 | DeFord et al. |
| 4,215,563 A | | 8/1980 | Clardy et al. |
| 4,357,668 A | * | 11/1982 | Schwartz et al. ............... 702/32 |
| 5,004,538 A | * | 4/1991 | Apfel ............... 210/198.2 |
| 5,311,444 A | | 5/1994 | Ohta |
| 5,478,751 A | | 12/1995 | Oosta et al. |
| 5,585,069 A | | 12/1996 | Zanzucchi et al. |
| 5,600,134 A | * | 2/1997 | Ashe et al. ............... 250/252.1 |

(Continued)

FOREIGN PATENT DOCUMENTS

EP 1 106 244 A2 6/2001

(Continued)

OTHER PUBLICATIONS

Fang, Liling et al., *High-throughput liquid chromatography ultra-violet/mass spectrometric analysis of combinatorial libraries using an eight-channel multiplexed electrospray time-of-flight mass spectrometer*, "Rapid Communicantions in Mass Spectrometry," vol. 16, pp. 1440-1447, John Wiley & Sons, Ltd., 2002.

(Continued)

*Primary Examiner*—Daniel S. Larkin
(74) *Attorney, Agent, or Firm*—Vincent K. Gustafson; Intellectual Property/Techology Law

(57) ABSTRACT

A parallel fluid processing system including multiple fluid process regions containing solid material in fluid communication with a common first fluid source may be used to conduct analyses and/or synthesis in parallel. A parallel fluid processing data correction method includes supplying and processing a calibrant in each fluid process region, measuring a first physical parameter and deriving at least one correction factor based on the parameter, supplying and processing at least one second fluid in each fluid process region, and then applying the correction factor to yield corrected process data. Retention time correction, peak area correction, and other useful data corrections may be performed. Parallel fluid processing may be performed with microfluidic devices and systems. A system for correcting retention times in parallel liquid chromatography is further provided.

44 Claims, 27 Drawing Sheets

U.S. PATENT DOCUMENTS

| | | | |
|---|---|---|---|
| 5,690,763 | A | 11/1997 | Ashmead et al. |
| 5,783,450 | A | 7/1998 | Yoshida et al. |
| 5,822,071 | A | 10/1998 | Dosmann et al. |
| 5,837,199 | A | 11/1998 | Dumschat |
| 5,849,208 | A | 12/1998 | Hayes et al. |
| 5,858,193 | A | 1/1999 | Zanzucchi et al. |
| 5,900,934 | A | 5/1999 | Gilby et al. |
| 5,987,959 | A * | 11/1999 | Klee et al. .................... 73/1.02 |
| 6,043,080 | A | 3/2000 | Lipshutz et al. |
| 6,258,263 | B1 | 7/2001 | Henderson et al. |
| 6,296,771 | B1 | 10/2001 | Miroslav |
| 6,309,541 | B1 | 10/2001 | Maiefski et al. |
| 6,331,439 | B1 | 12/2001 | Cherukuri et al. |
| 6,369,893 | B1 | 4/2002 | Christel et al. |
| 6,430,512 | B1 | 8/2002 | Gallagher |
| 6,436,292 | B1 | 8/2002 | Petro |
| 6,461,515 | B1 | 10/2002 | Safir et al. |
| 6,508,938 | B2 | 1/2003 | Maiefski et al. |
| 6,532,978 | B1 | 3/2003 | Müller-Kuhrt et al. |
| 6,537,501 | B1 | 3/2003 | Holl et al. |
| 6,572,830 | B1 | 6/2003 | Burdon et al. |
| 6,581,441 | B1 | 6/2003 | Paul |
| 6,660,149 | B1 | 12/2003 | Karger et al. |
| 6,691,053 | B2 | 2/2004 | Quimby et al. ............... 702/89 |
| 6,802,969 | B2 | 10/2004 | Tanimura ................. 210/198.2 |
| 2002/0033336 | A1 | 3/2002 | Liu et al. |
| 2002/0068366 | A1 | 6/2002 | LaDine et al. |
| 2002/0158022 | A1 | 10/2002 | Huang et al. |
| 2002/0189947 | A1 | 12/2002 | Paul et al. |
| 2003/0089663 | A1 | 5/2003 | Petro et al. |
| 2003/0118486 | A1 | 6/2003 | Zhou et al. |
| 2003/0158716 | A1 | 8/2003 | Kuderer |

FOREIGN PATENT DOCUMENTS

| | | |
|---|---|---|
| JP | 02-157714 | 6/1990 |
| JP | 07103959 A2 | 4/1995 |
| WO | WO 94/21372 | 9/1994 |
| WO | WO 97/30347 | 8/1997 |
| WO | WO 98/09315 | 3/1998 |
| WO | WO 00/31528 | 6/2000 |
| WO | WO 00/51720 A3 | 9/2000 |
| WO | WO 00/76662 A2 | 12/2000 |
| WO | WO 02/48684 A2 | 6/2002 |
| WO | WO 02/056006 A2 | 7/2002 |

OTHER PUBLICATIONS

Wrotnowski, Cort, Capillary Electrophoresis For Proteomics Projects, "Genetic Engineering News," vol. 23, No. 1, Jan. 1, 2003.

Chang, Gue Su, "Theoretical Considerations: Quantification Methods in Chromatography," Web document available at http://gc.discussing.info/gs/b_theory/quantification_method.html, downloaded Apr. 9, 2002.

Tolson, David et al., *Development of high-pressure gradient pumping system for parallel liquid chromatography/mass spectrometry for the analysis of combinatorial libraries*, RCM Letter to the Editor, "Rapid Communications in Mass Spectrometry," 2001, vol. 15, pp. 1244-1249.

Córdova, Emilio et al., *Noncovalent Polycationic Coatings for Capillaries in Capillary Electrophoresis of Proteins*, "Analytical Chemistry," vol. 69, No. 7, Apr. 1, 1997.

Palm, Anders et al., "Integrated Sample Preparation and MALDI MS on a disc," *Micro Total Analysis Systems*, 2001, pp. 216-218, J.M. Ramsey and A. van den Berg (eds.), Kluwer Academic Publishers in the Netherlands.

Duffy, David C. et al., *Rapid Prototyping of Microfluidic Systems in Poly(dimethylsiloxane)*, "Analytical Chemistry," vol. 70, No. 23, Dec. 1, 1998.

Dunn, John A. et al., "A Parallel LC/MS/MS System for the High Throughput Quantification of Clinical Trial Samples. A Validation Study," Waters Application Note, Oct. 2002.

Metz, Stefan et al., "Flexible Polyimide-Based Microchannels with Embedded Microelectrodes," *Micro Total Analysis Systems*, 2001, pp. 171-172, J.M. Ramsey and A. van den Berg (eds.), Kluwer Academic Publishers in the Netherlands.

Poole, Colin F., *1.8.1 Signal Characteristics*, "1.8 Principles of Quantification," *The Essence of Chromatography*, 2003, Elsevier Science B. V., Amsterdam, The Netherlands, pp. 63-78.

Snyder, Lloyd R., et al., *Practical HPLC Method Development, Second Edition*, 1997, John Wiley & Sons, Inc., pp. 653-660.

* cited by examiner

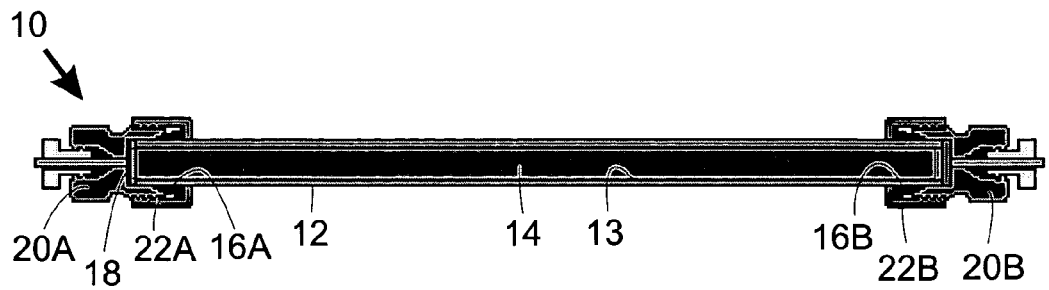
FIG. _1 (PRIOR ART)
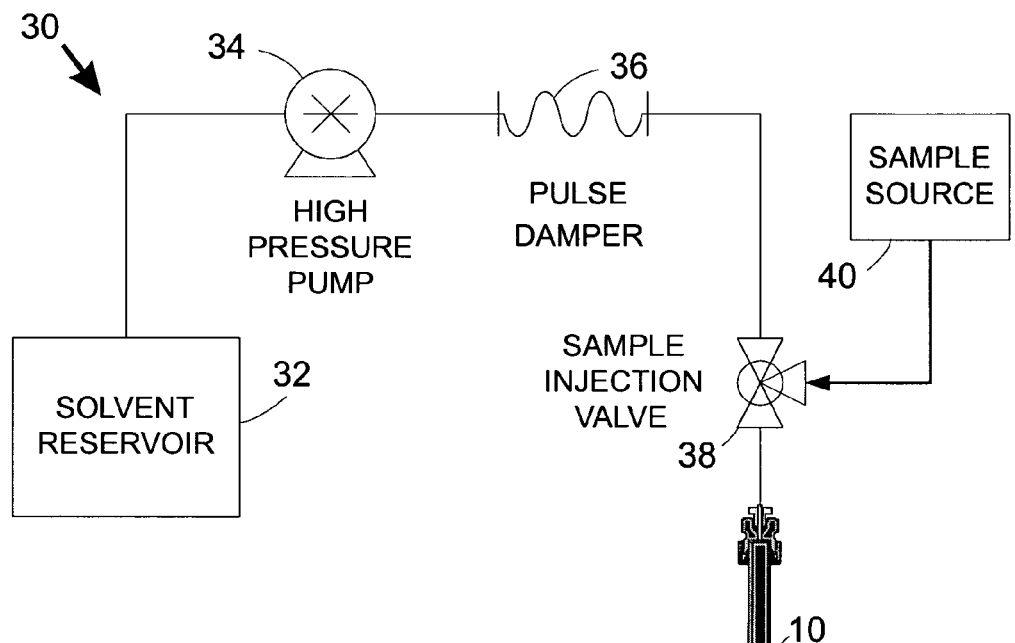
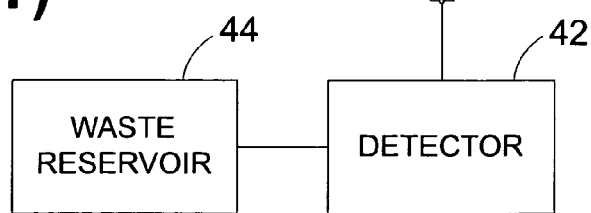
FIG. _2 (PRIOR ART)

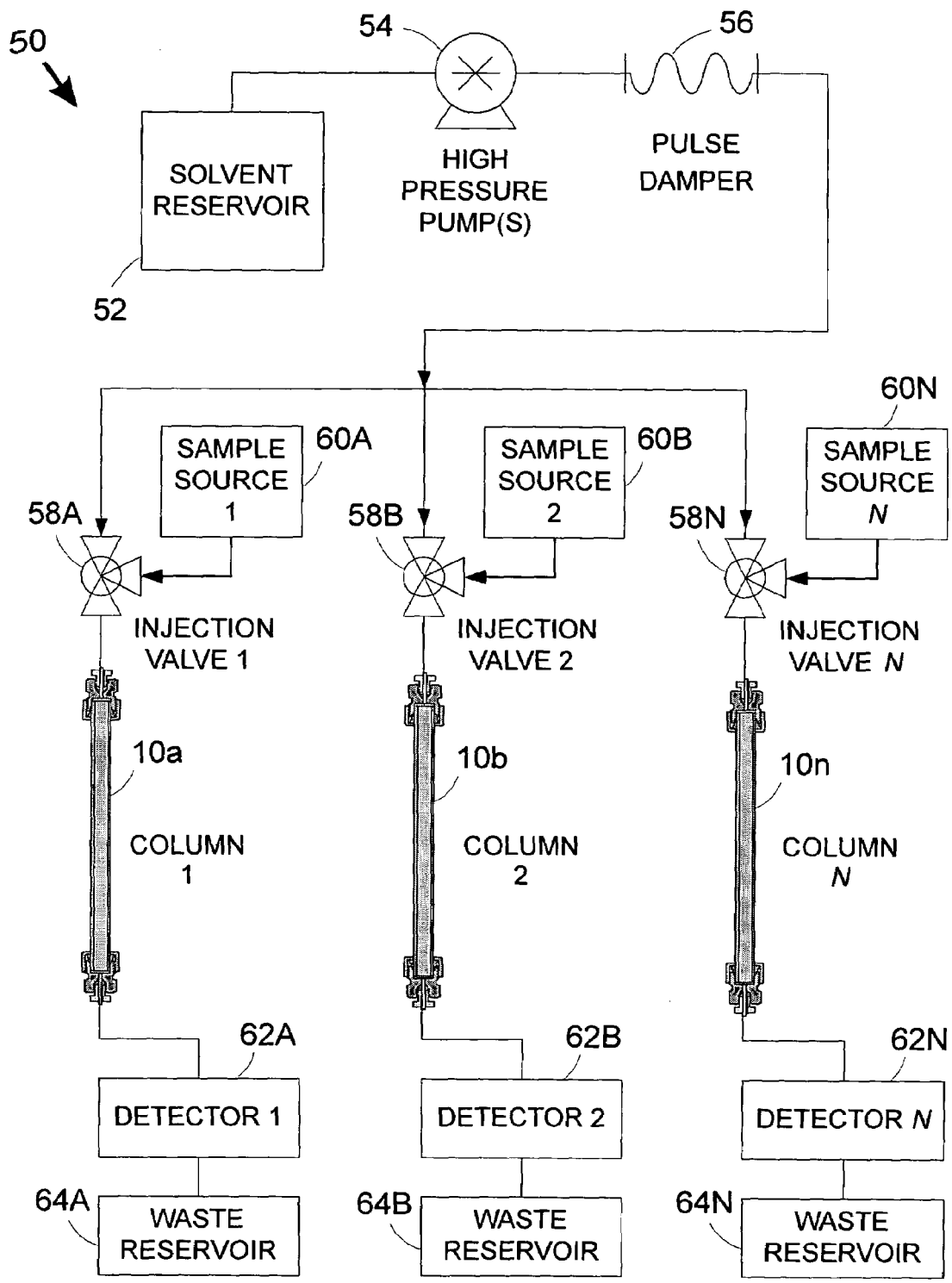
FIG. _3 (PRIOR ART)

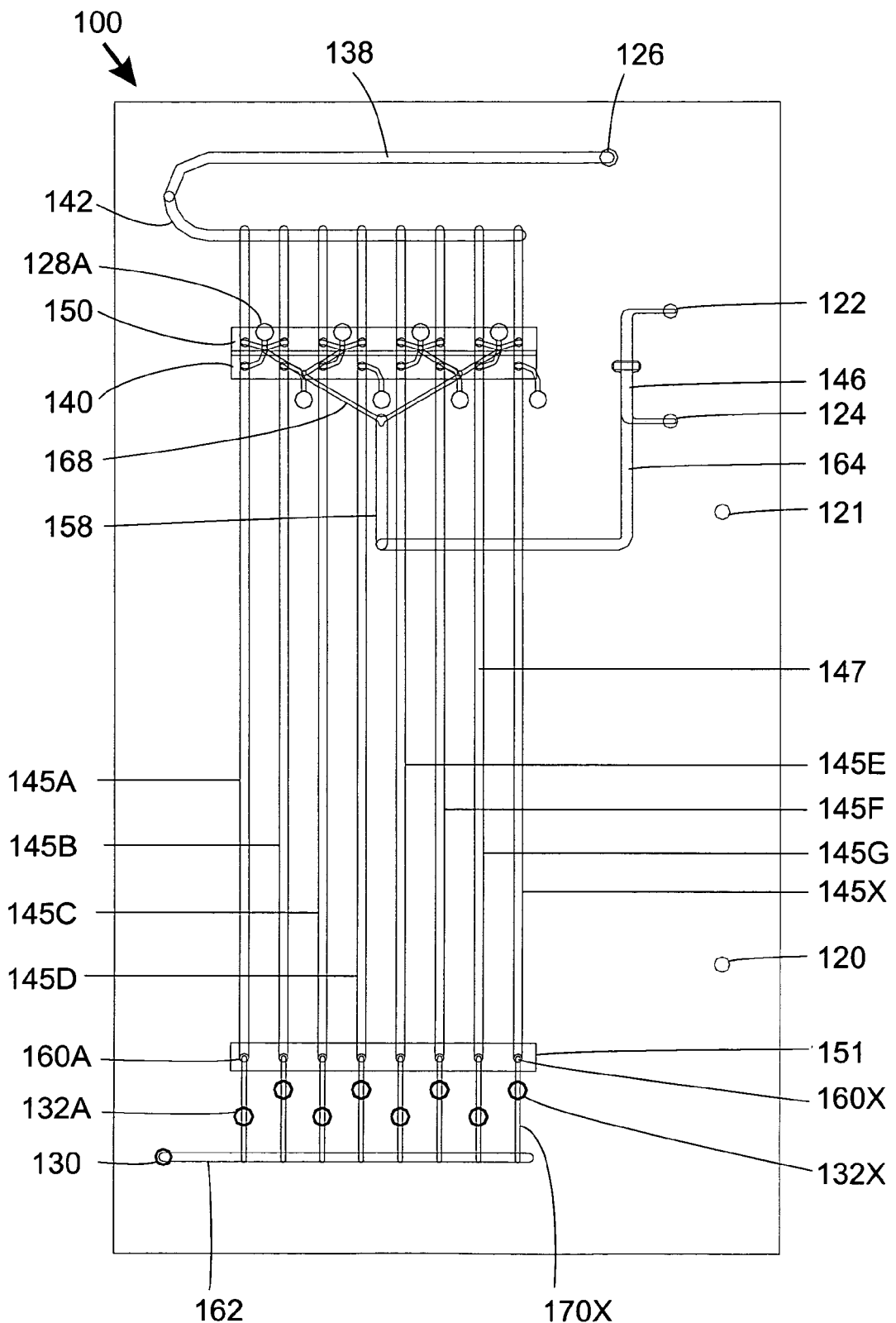
FIG._4B

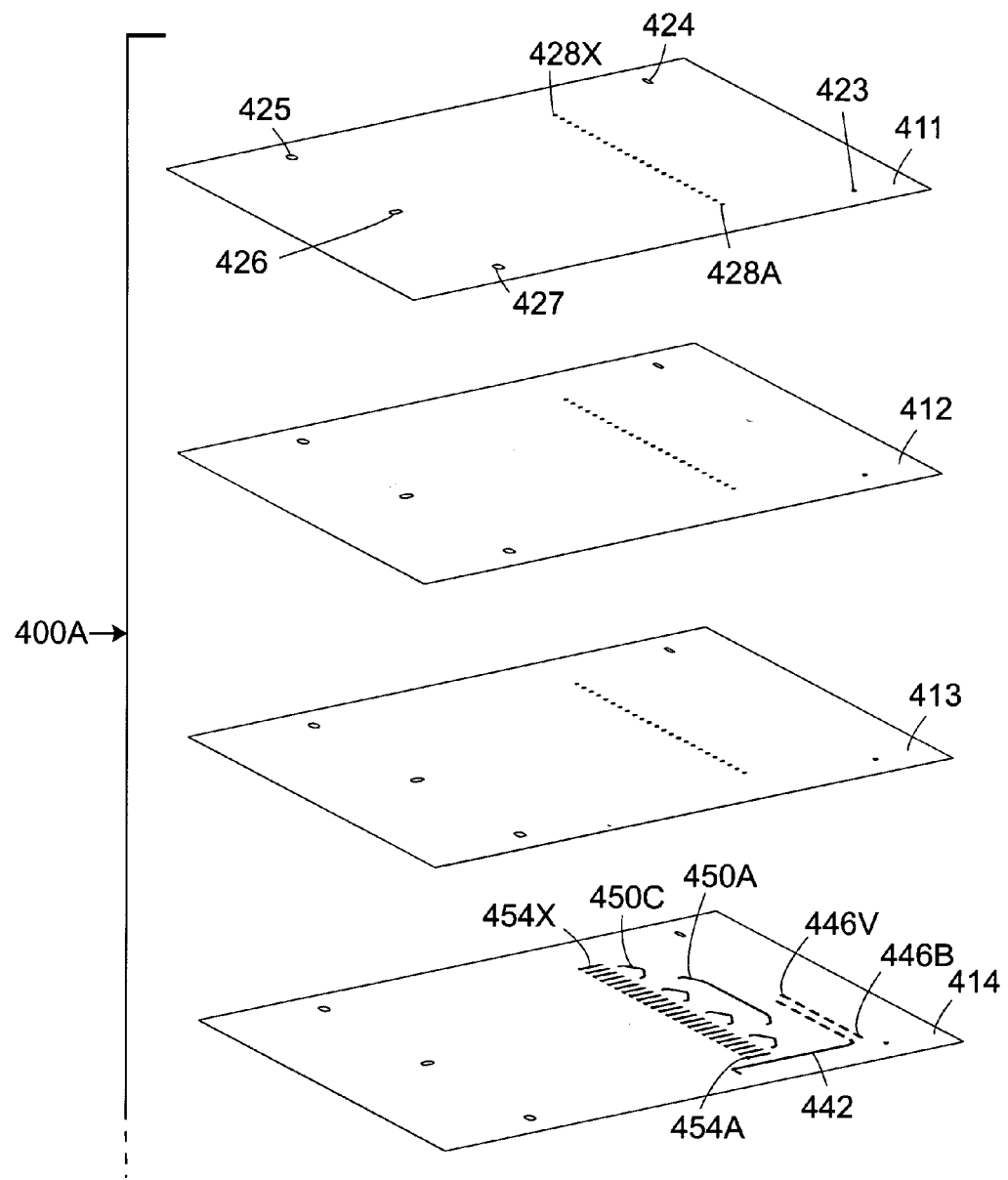
FIG._6A

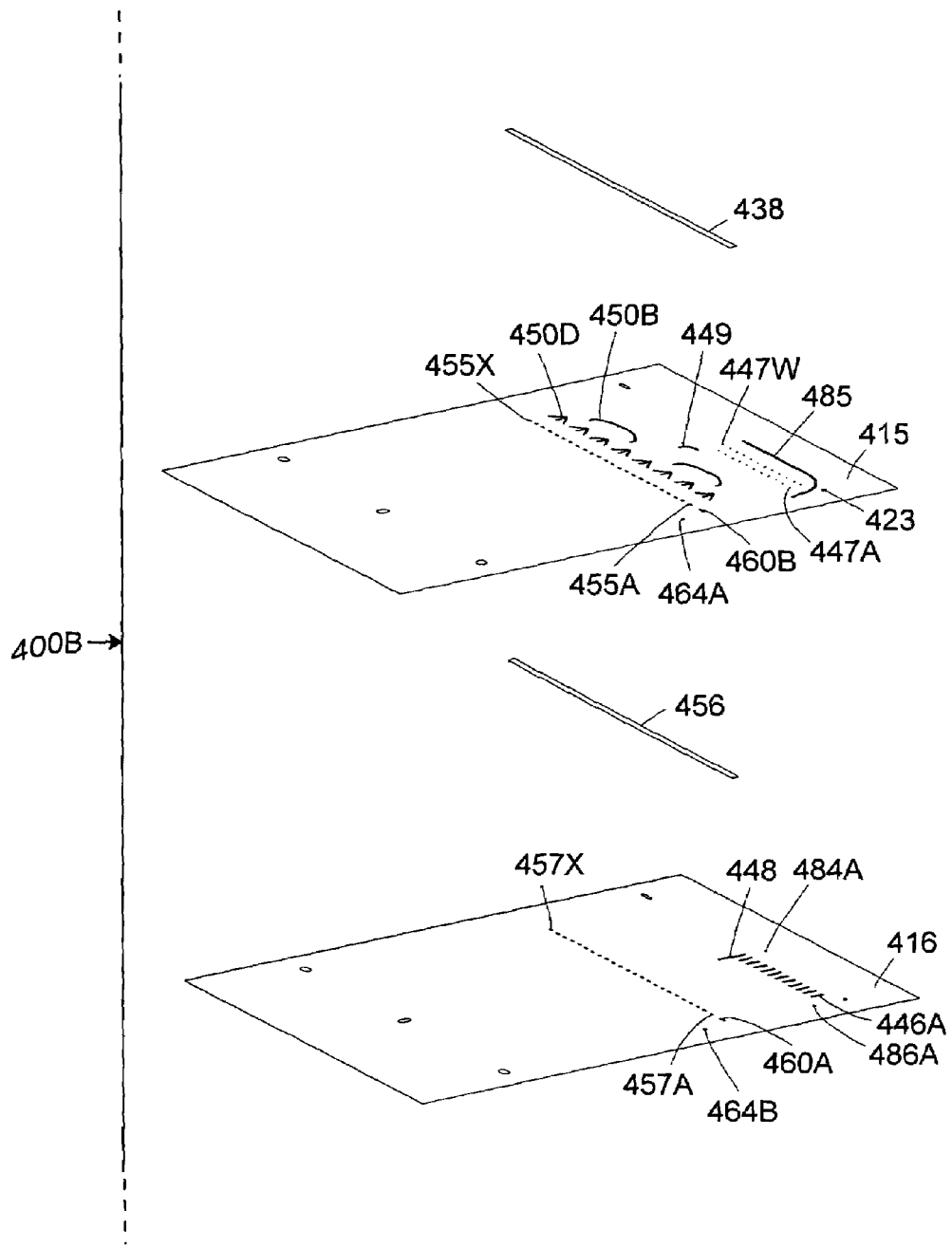
FIG._6B

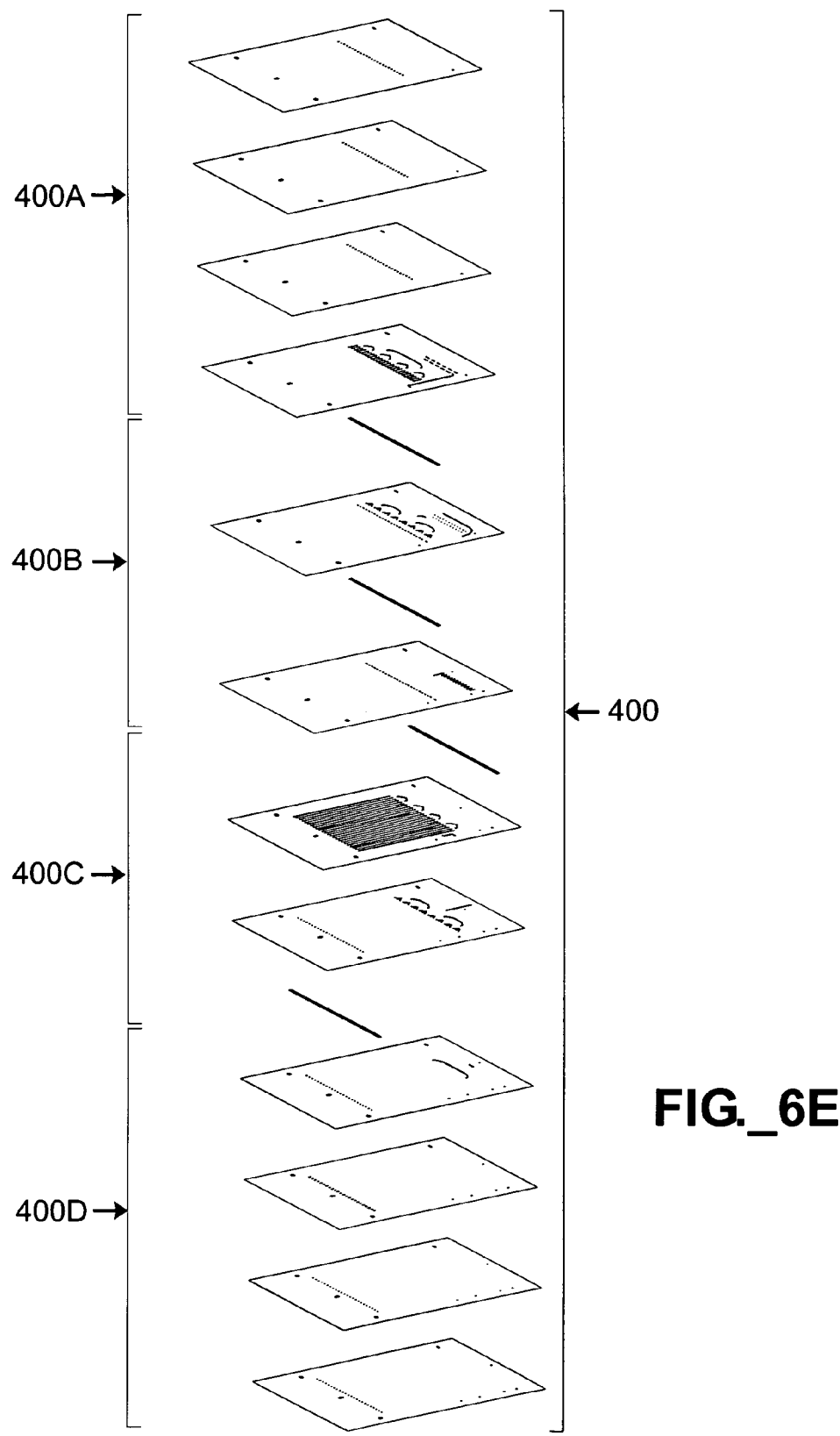
FIG._6E

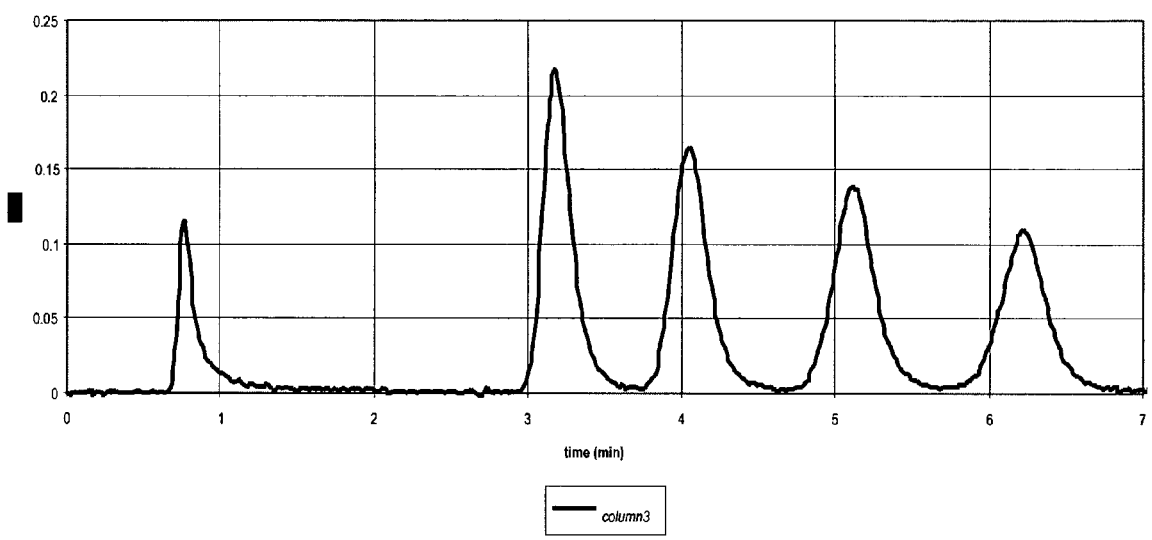
FIG. _7

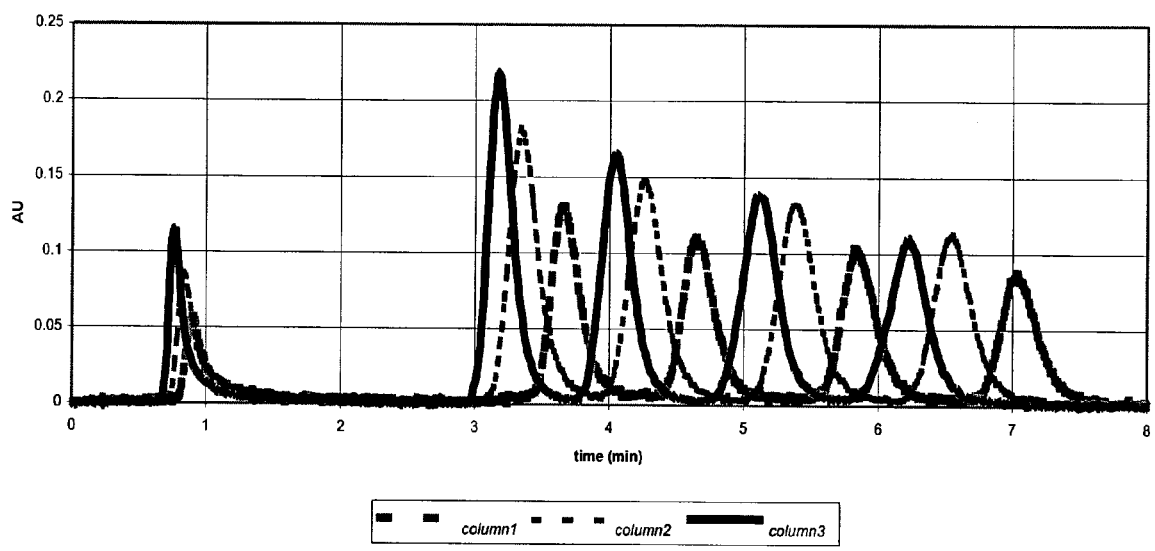
FIG._8

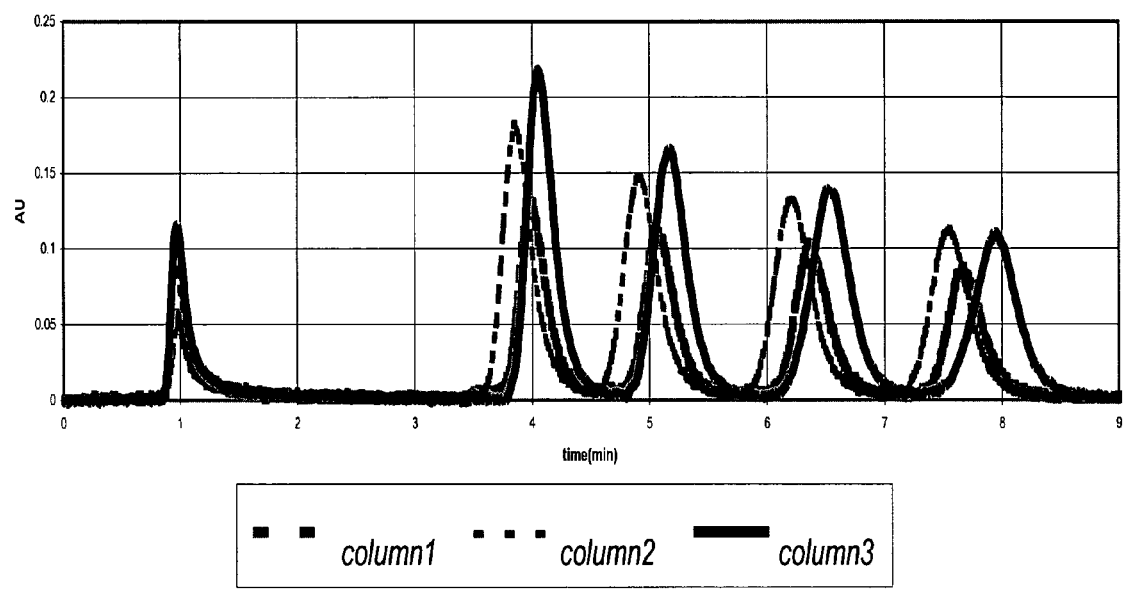
FIG._9

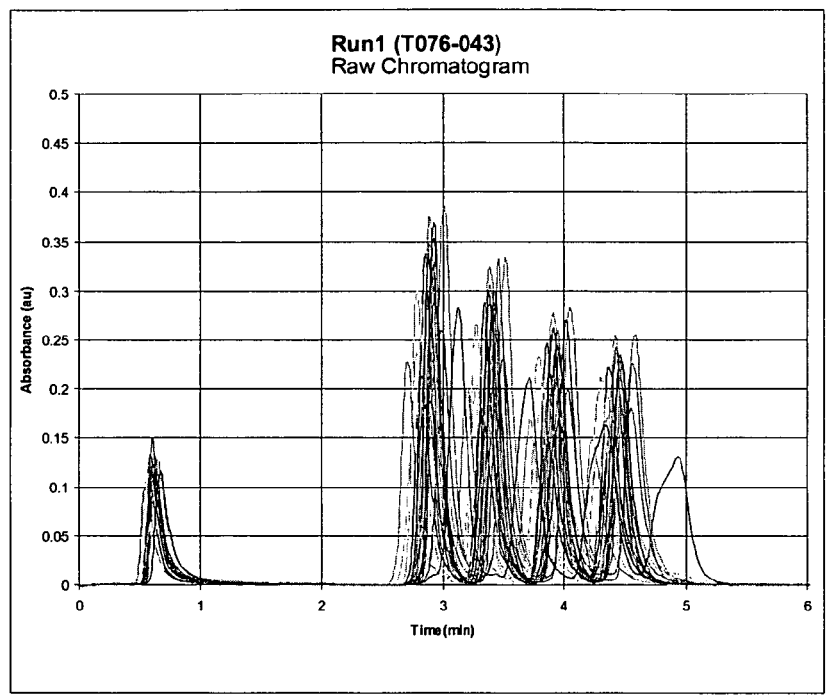
FIG._10
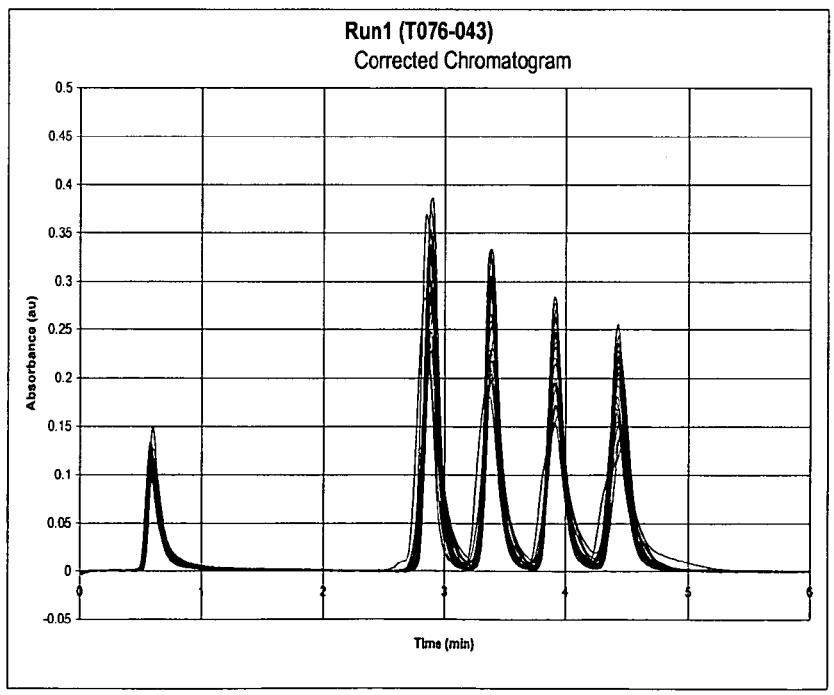
FIG._11

| RAW Run1 (reference run) | | | | | |
|---|---|---|---|---|---|
| Colum # | Pk1 | Pk2 | Pk3 | Pk4 | Pk5 |
| 1 | 0.633 | 3 | 3.5 | 4.033 | 4.55 |
| 2 | 0.567 | 2.783 | 3.283 | 3.8 | 4.317 |
| 3 | 0.55 | 2.7 | 3.2 | 3.717 | 4.233 |
| 4 | 0.583 | 2.85 | 3.367 | 3.883 | 4.4 |
| 5 | 0.6 | 2.833 | 3.333 | 3.867 | 4.383 |
| 6 | 0.633 | 2.933 | 3.433 | 3.967 | 4.483 |
| 7 | 0.6 | 2.85 | 3.35 | 3.867 | 4.367 |
| 8 | 0.6 | 2.867 | 3.383 | 3.883 | 4.367 |
| 9 | 0.583 | 2.833 | 3.333 | 3.85 | 4.367 |
| 10 | 0.6 | 2.883 | 3.383 | 3.917 | 4.417 |
| 11 | 0.567 | 2.783 | 3.283 | 3.8 | 4.3 |
| 12 | 0.633 | 2.95 | 3.45 | 3.967 | 4.483 |
| 13 | 0.65 | 3.017 | 3.517 | 4.05 | 4.583 |
| 14 | 0.617 | 2.9 | 3.383 | 3.917 | 4.417 |
| 15 | 0.583 | 2.783 | 3.283 | 3.8 | 4.3 |
| 16 | 0.633 | 2.917 | 3.417 | 3.95 | 4.467 |
| 17 | 0.617 | 2.9 | 3.383 | 3.917 | 4.433 |
| 18 | 0.617 | 2.917 | 3.417 | 3.95 | 4.467 |
| 19 | 0.633 | 2.933 | 3.433 | 3.967 | 4.483 |
| 20 | 0.617 | 2.883 | 3.383 | 3.917 | 4.433 |
| 21 | 0.6 | 2.883 | 3.383 | 3.933 | 4.45 |
| 22 | 0.617 | 2.917 | 3.467 | 4.033 | 4.567 |
| 23 | 0.633 | 2.933 | 3.433 | 3.95 | 4.467 |
| 24 | 0.683 | 3.117 | 3.7 | 4.333 | 4.917 |
| AVG Peak | 0.610 | 2.890 | 3.396 | 3.928 | 4.444 |

FIG._12A

| COEFFICIENTS | | (a+bx) |
|---|---|---|
| | | |
| 1 | -0.019 | 0.977 |
| 2 | 0.034 | 1.024 |
| 3 | 0.049 | 1.043 |
| 4 | 0.024 | 1.004 |
| 5 | 0.007 | 1.014 |
| 6 | -0.022 | 0.996 |
| 7 | -0.003 | 1.017 |
| 8 | -0.008 | 1.014 |
| 9 | 0.019 | 1.014 |
| 10 | 0.005 | 1.003 |
| 11 | 0.029 | 1.026 |
| 12 | -0.028 | 0.995 |
| 13 | -0.031 | 0.975 |
| 14 | -0.017 | 1.008 |
| 15 | 0.012 | 1.031 |
| 16 | -0.023 | 1.000 |
| 17 | -0.013 | 1.005 |
| 18 | -0.007 | 0.996 |
| 19 | -0.022 | 0.996 |
| 20 | -0.008 | 1.005 |
| 21 | 0.016 | 0.996 |
| 22 | 0.026 | 0.970 |
| 23 | -0.029 | 1.000 |
| 24 | 0.016 | 0.907 |
| AVG | 0.000 | 1.001 |

FIG._12B

| CORRECTED Run1 (reference run) | | | | | |
|---|---|---|---|---|---|
| Colum # | Pk1 | Pk2 | Pk3 | Pk4 | Pk5 |
| 1 | 0.600 | 2.914 | 3.402 | 3.923 | 4.429 |
| 2 | 0.614 | 2.883 | 3.394 | 3.924 | 4.453 |
| 3 | 0.623 | 2.866 | 3.387 | 3.927 | 4.465 |
| 4 | 0.610 | 2.886 | 3.405 | 3.924 | 4.443 |
| 5 | 0.616 | 2.881 | 3.388 | 3.930 | 4.453 |
| 6 | 0.608 | 2.897 | 3.395 | 3.927 | 4.441 |
| 7 | 0.607 | 2.894 | 3.402 | 3.928 | 4.436 |
| 8 | 0.600 | 2.898 | 3.422 | 3.928 | 4.419 |
| 9 | 0.610 | 2.891 | 3.398 | 3.922 | 4.446 |
| 10 | 0.607 | 2.896 | 3.398 | 3.933 | 4.434 |
| 11 | 0.611 | 2.886 | 3.399 | 3.930 | 4.443 |
| 12 | 0.602 | 2.908 | 3.405 | 3.920 | 4.433 |
| 13 | 0.603 | 2.911 | 3.398 | 3.918 | 4.438 |
| 14 | 0.605 | 2.906 | 3.392 | 3.931 | 4.435 |
| 15 | 0.613 | 2.882 | 3.397 | 3.930 | 4.446 |
| 16 | 0.610 | 2.894 | 3.394 | 3.927 | 4.444 |
| 17 | 0.608 | 2.903 | 3.388 | 3.925 | 4.444 |
| 18 | 0.608 | 2.898 | 3.395 | 3.926 | 4.441 |
| 19 | 0.608 | 2.897 | 3.395 | 3.927 | 4.441 |
| 20 | 0.612 | 2.889 | 3.392 | 3.928 | 4.447 |
| 21 | 0.614 | 2.887 | 3.385 | 3.933 | 4.448 |
| 22 | 0.624 | 2.856 | 3.390 | 3.939 | 4.458 |
| 23 | 0.604 | 2.903 | 3.403 | 3.920 | 4.437 |
| 24 | 0.636 | 2.842 | 3.371 | 3.945 | 4.474 |
| AVG Peak | 0.610 | 2.890 | 3.396 | 3.928 | 4.444 |

FIG._12C

| Colum # | Pk1 | Pk2 | Pk3 | Pk4 | Pk5 |
|---|---|---|---|---|---|
| 1 | 0.633 | 3 | 3.517 | 4.05 | 4.567 |
| 2 | 0.567 | 2.783 | 3.283 | 3.8 | 4.317 |
| 3 | 0.55 | 2.717 | 3.217 | 3.733 | 4.25 |
| 4 | 0.6 | 2.867 | 3.367 | 3.883 | 4.4 |
| 5 | 0.6 | 2.8 | 3.317 | 3.833 | 4.367 |
| 6 | 0.633 | 2.95 | 3.45 | 3.967 | 4.483 |
| 7 | 0.6 | 2.867 | 3.367 | 3.883 | 4.383 |
| 8 | 0.6 | 2.8 | 3.283 | 3.817 | 4.317 |
| 9 | 0.6 | 2.85 | 3.35 | 3.867 | 4.367 |
| 10 | 0.617 | 2.9 | 3.4 | 3.933 | 4.433 |
| 11 | 0.6 | 2.8 | 3.283 | 3.8 | 4.317 |
| 12 | 0.65 | 2.95 | 3.45 | 3.983 | 4.483 |
| 13 | 0.667 | 3.017 | 3.517 | 4.05 | 4.583 |
| 14 | 0.633 | 2.9 | 3.4 | 3.917 | 4.433 |
| 15 | 0.6 | 2.8 | 3.283 | 3.8 | 4.317 |
| 16 | 0.633 | 2.933 | 3.433 | 3.95 | 4.467 |
| 17 | 0.633 | 2.9 | 3.4 | 3.933 | 4.433 |
| 18 | 0.633 | 2.933 | 3.433 | 3.95 | 4.467 |
| 19 | 0.65 | 2.95 | 3.45 | 3.983 | 4.5 |
| 20 | 0.633 | 2.883 | 3.383 | 3.917 | 4.433 |
| 21 | 0.6 | 2.867 | 3.383 | 3.917 | 4.45 |
| 22 | 0.617 | 2.917 | 3.467 | 4.033 | 4.583 |
| 23 | 0.633 | 2.933 | 3.433 | 3.967 | 4.483 |
| 24 | 0.683 | 3.117 | 3.717 | 4.333 | 4.933 |
| AVG | 0.619 | 2.893 | 3.399 | 3.929 | 4.449 |

FIG._12D

| Colum # | Pk1 | Pk2 | Pk3 | Pk4 | Pk5 |
|---|---|---|---|---|---|
| 1 | 0.600 | 2.914 | 3.419 | 3.940 | 4.445 |
| 2 | 0.614 | 2.883 | 3.394 | 3.924 | 4.453 |
| 3 | 0.623 | 2.884 | 3.405 | 3.943 | 4.483 |
| 4 | 0.627 | 2.903 | 3.405 | 3.924 | 4.443 |
| 5 | 0.616 | 2.847 | 3.372 | 3.895 | 4.437 |
| 6 | 0.608 | 2.914 | 3.412 | 3.927 | 4.441 |
| 7 | 0.607 | 2.911 | 3.420 | 3.944 | 4.453 |
| 8 | 0.600 | 2.831 | 3.320 | 3.862 | 4.368 |
| 9 | 0.627 | 2.908 | 3.415 | 3.939 | 4.446 |
| 10 | 0.624 | 2.913 | 3.415 | 3.949 | 4.450 |
| 11 | 0.645 | 2.903 | 3.399 | 3.930 | 4.460 |
| 12 | 0.619 | 2.908 | 3.405 | 3.936 | 4.433 |
| 13 | 0.619 | 2.911 | 3.398 | 3.918 | 4.438 |
| 14 | 0.621 | 2.906 | 3.410 | 3.931 | 4.451 |
| 15 | 0.631 | 2.899 | 3.397 | 3.930 | 4.463 |
| 16 | 0.610 | 2.910 | 3.410 | 3.927 | 4.444 |
| 17 | 0.624 | 2.903 | 3.405 | 3.941 | 4.444 |
| 18 | 0.624 | 2.914 | 3.411 | 3.926 | 4.441 |
| 19 | 0.625 | 2.914 | 3.412 | 3.943 | 4.458 |
| 20 | 0.628 | 2.889 | 3.392 | 3.928 | 4.447 |
| 21 | 0.614 | 2.872 | 3.385 | 3.917 | 4.448 |
| 22 | 0.624 | 2.856 | 3.390 | 3.939 | 4.473 |
| 23 | 0.604 | 2.903 | 3.403 | 3.937 | 4.453 |
| 24 | 0.636 | 2.842 | 3.386 | 3.945 | 4.489 |
| AVG Peak | 0.620 | 2.893 | 3.399 | 3.929 | 4.448 |

FIG._12E

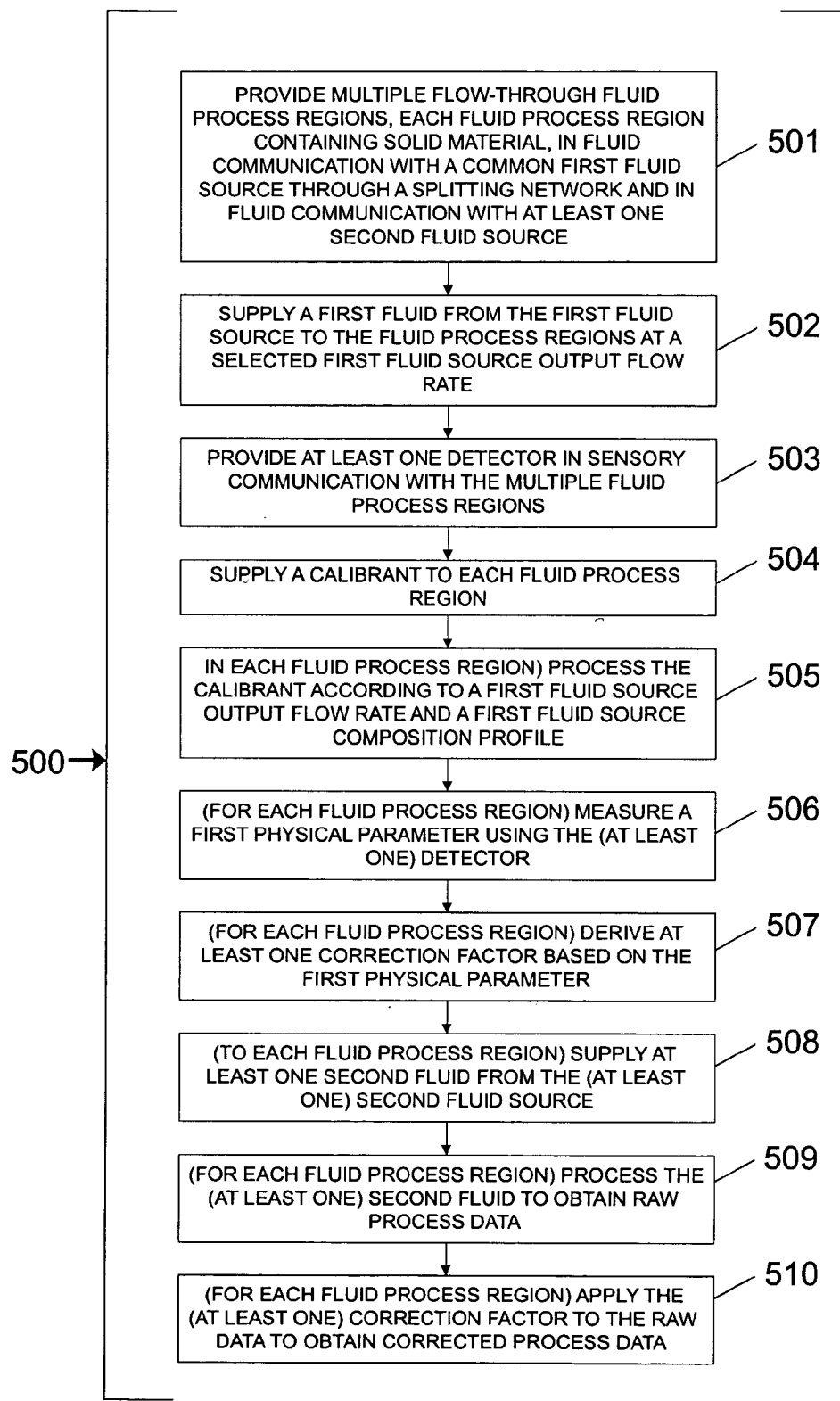
FIG._13

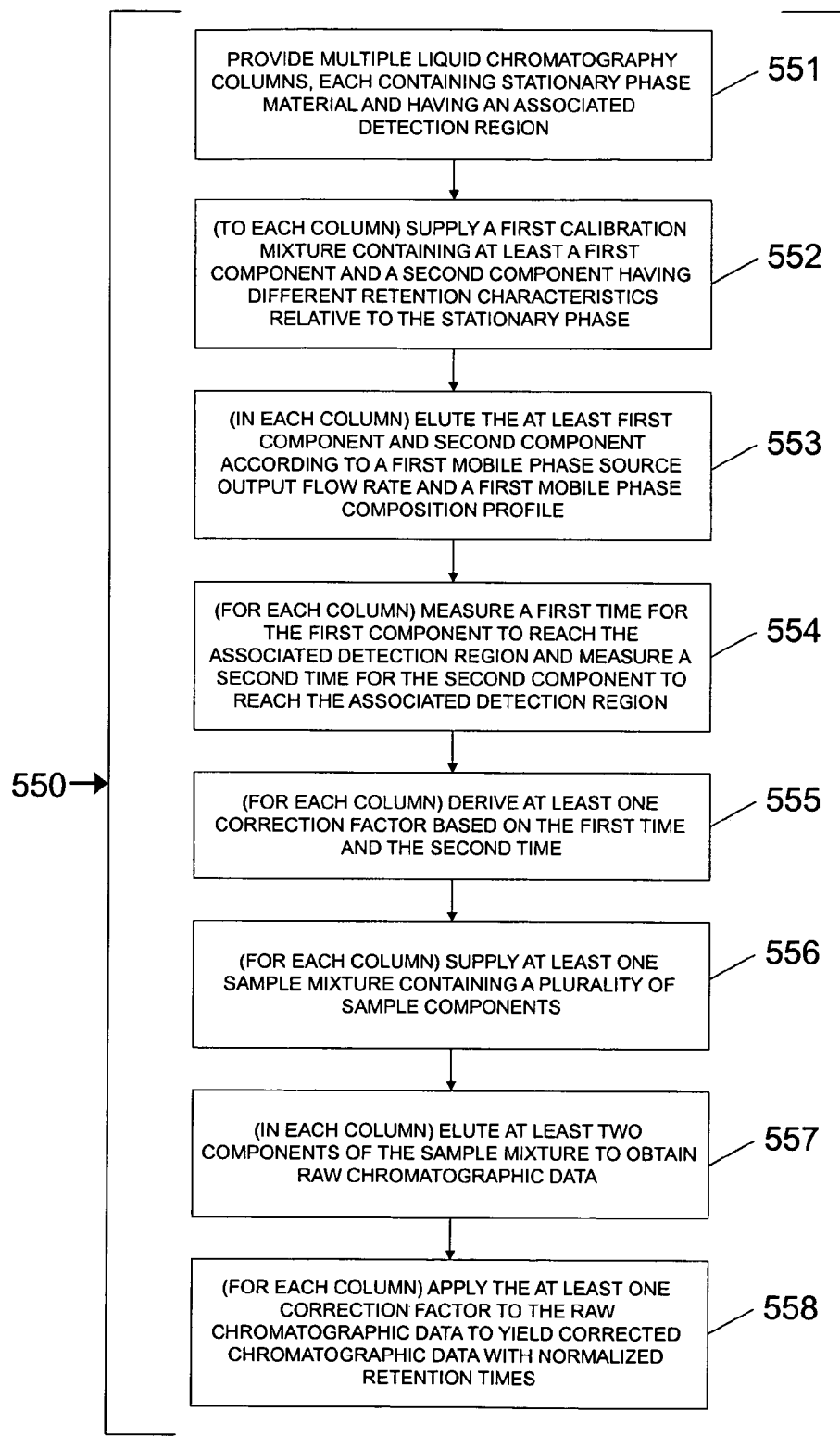
FIG._14

Run 1: Peak Area Data & Derivation of Correction Factors

| Column Number | Peak 2 Area (Raw) | Peak 3 Area (Raw) | Peak 4 Area (Raw) | Peak 5 Area (Raw) | Average Area: Peaks 2-5 (single column) | Average Area: Peaks 2-5 (all columns) | Correction Factor |
|---|---|---|---|---|---|---|---|
| 1 | 122.3 | 108.9 | 95.8 | 88.7 | 103.9 | 105.9 | 1.019 |
| 2 | 118.0 | 104.8 | 96.7 | 88.9 | 102.1 | 105.9 | 1.038 |
| 3 | 114.9 | 102.1 | 91.4 | 83.7 | 98.1 | 105.9 | 1.080 |
| 4 | 105.3 | 93.0 | 80.3 | 74.8 | 88.3 | 105.9 | 1.199 |
| 5 | 126.9 | 111.3 | 98.4 | 90.2 | 106.7 | 105.9 | 0.993 |
| 6 | 119.1 | 106.1 | 93.9 | 86.9 | 101.5 | 105.9 | 1.044 |
| 7 | 144.2 | 135.4 | 118.5 | 103.9 | 125.5 | 105.9 | 0.844 |
| 8 | 118.7 | 105.5 | 91.3 | 82.9 | 99.6 | 105.9 | 1.064 |
| 9 | 121.3 | 113.1 | 97.6 | 84.1 | 104.0 | 105.9 | 1.018 |
| 10 | 137.6 | 129.5 | 109.1 | 90.8 | 116.7 | 105.9 | 0.907 |
| 11 | 144.6 | 129.4 | 112.3 | 103.2 | 122.4 | 105.9 | 0.866 |
| 12 | 121.4 | 109.1 | 94.6 | 88.6 | 103.4 | 105.9 | 1.024 |
| 13 | 129.5 | 122.8 | 109.4 | 97.1 | 114.7 | 105.9 | 0.924 |
| 14 | 130.1 | 123.1 | 107.8 | 94.4 | 113.9 | 105.9 | 0.930 |
| 15 | 114.9 | 106.0 | 90.9 | 80.8 | 98.1 | 105.9 | 1.079 |
| 16 | 114.9 | 100.8 | 86.9 | 78.3 | 95.2 | 105.9 | 1.113 |
| 17 | 134.9 | 119.5 | 105.6 | 96.1 | 114.0 | 105.9 | 0.929 |
| 18 | 120.3 | 106.9 | 93.4 | 84.9 | 101.4 | 105.9 | 1.045 |
| 19 | 130.3 | 115.8 | 102.3 | 94.0 | 110.6 | 105.9 | 0.958 |
| 20 | 115.0 | 102.1 | 90.7 | 84.0 | 97.9 | 105.9 | 1.082 |
| 21 | 124.4 | 110.2 | 97.9 | 89.3 | 105.4 | 105.9 | 1.005 |
| 22 | 123.7 | 109.4 | 96.3 | 87.8 | 104.3 | 105.9 | 1.016 |
| 23 | 124.9 | 111.4 | 97.6 | 89.7 | 105.9 | 105.9 | 1.000 |
| 24 | 126.7 | 113.1 | 100.9 | 93.7 | 108.6 | 105.9 | 0.975 |

FIG. 15A

Run 2: Peak 3 Area Correction

| Column Number | Correction Factor | Peak 3 Area (Raw) | Peak 3 Area (Corrected) |
|---|---|---|---|
| 1 | 1.019 | 116.0 | 118.3 |
| 2 | 1.038 | 106.5 | 110.5 |
| 3 | 1.080 | 106.7 | 115.3 |
| 4 | 1.199 | 95.4 | 114.4 |
| 5 | 0.993 | 118.9 | 118.0 |
| 6 | 1.044 | 101.8 | 106.2 |
| 7 | 0.844 | 135.5 | 114.3 |
| 8 | 1.064 | 104.9 | 111.5 |
| 9 | 1.018 | 113.2 | 115.2 |
| 10 | 0.907 | 131.5 | 119.3 |
| 11 | 0.866 | 130.6 | 113.0 |
| 12 | 1.024 | 110.3 | 112.9 |
| 13 | 0.924 | 122.3 | 112.9 |
| 14 | 0.930 | 118.2 | 110.0 |
| 15 | 1.079 | 113.3 | 122.4 |
| 16 | 1.113 | 100.7 | 112.1 |
| 17 | 0.929 | 117.4 | 109.0 |
| 18 | 1.045 | 107.3 | 112.2 |
| 19 | 0.958 | 112.7 | 108.0 |
| 20 | 1.082 | 105.1 | 113.6 |
| 21 | 1.005 | 112.1 | 112.6 |
| 22 | 1.016 | 108.8 | 110.5 |
| 23 | 1.000 | 110.0 | 110.1 |
| 24 | 0.975 | 115.8 | 113.0 |
| | %CV | 8.7 | 3.3 |

FIG. 15B

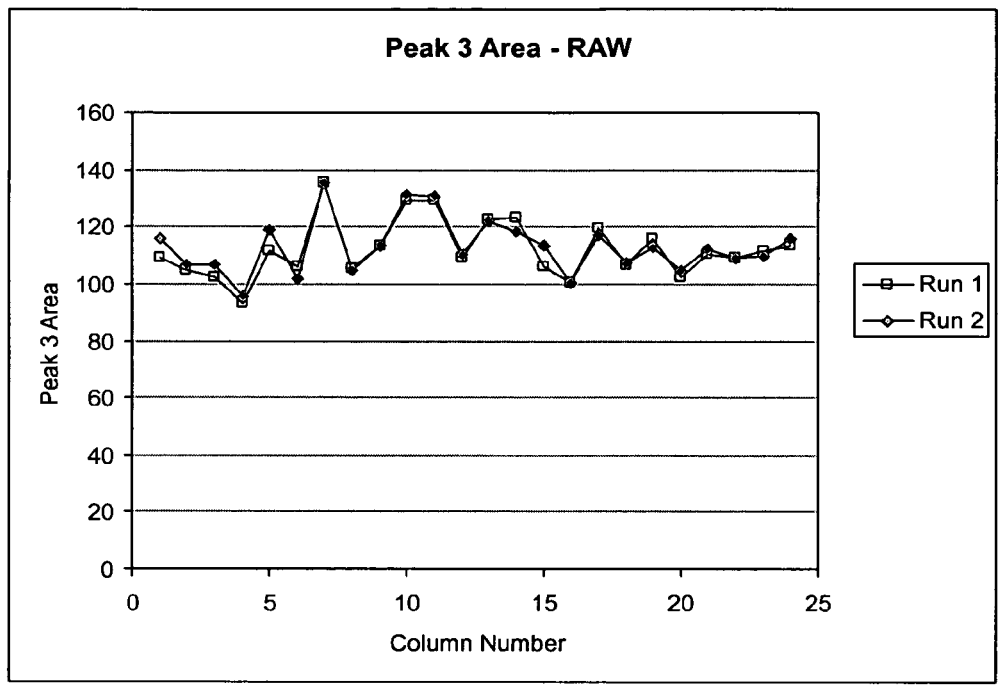
FIG._16A
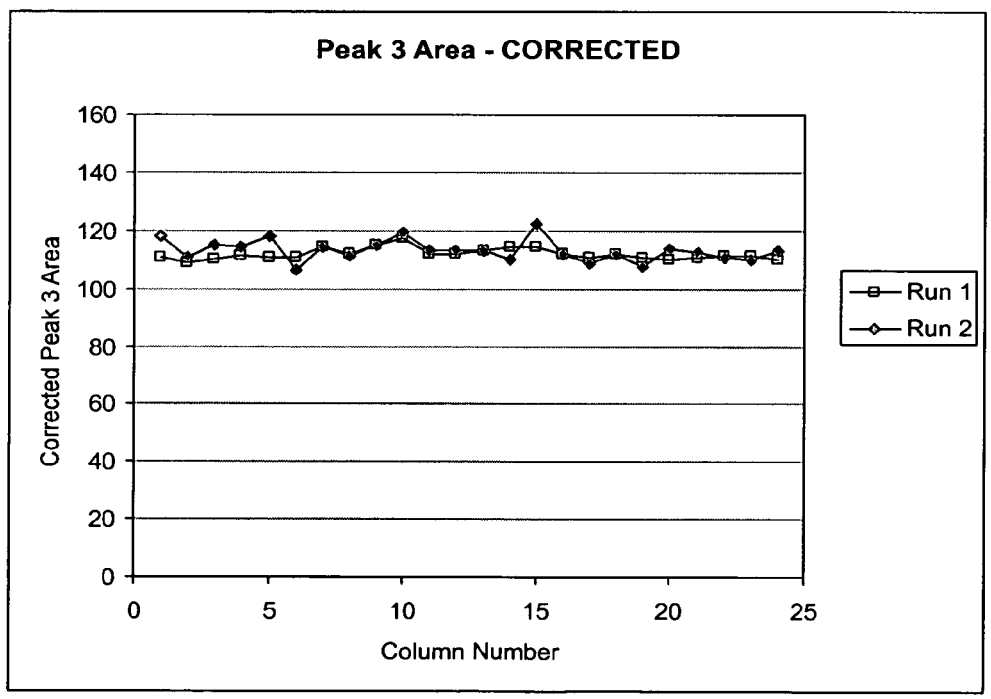
FIG._16B

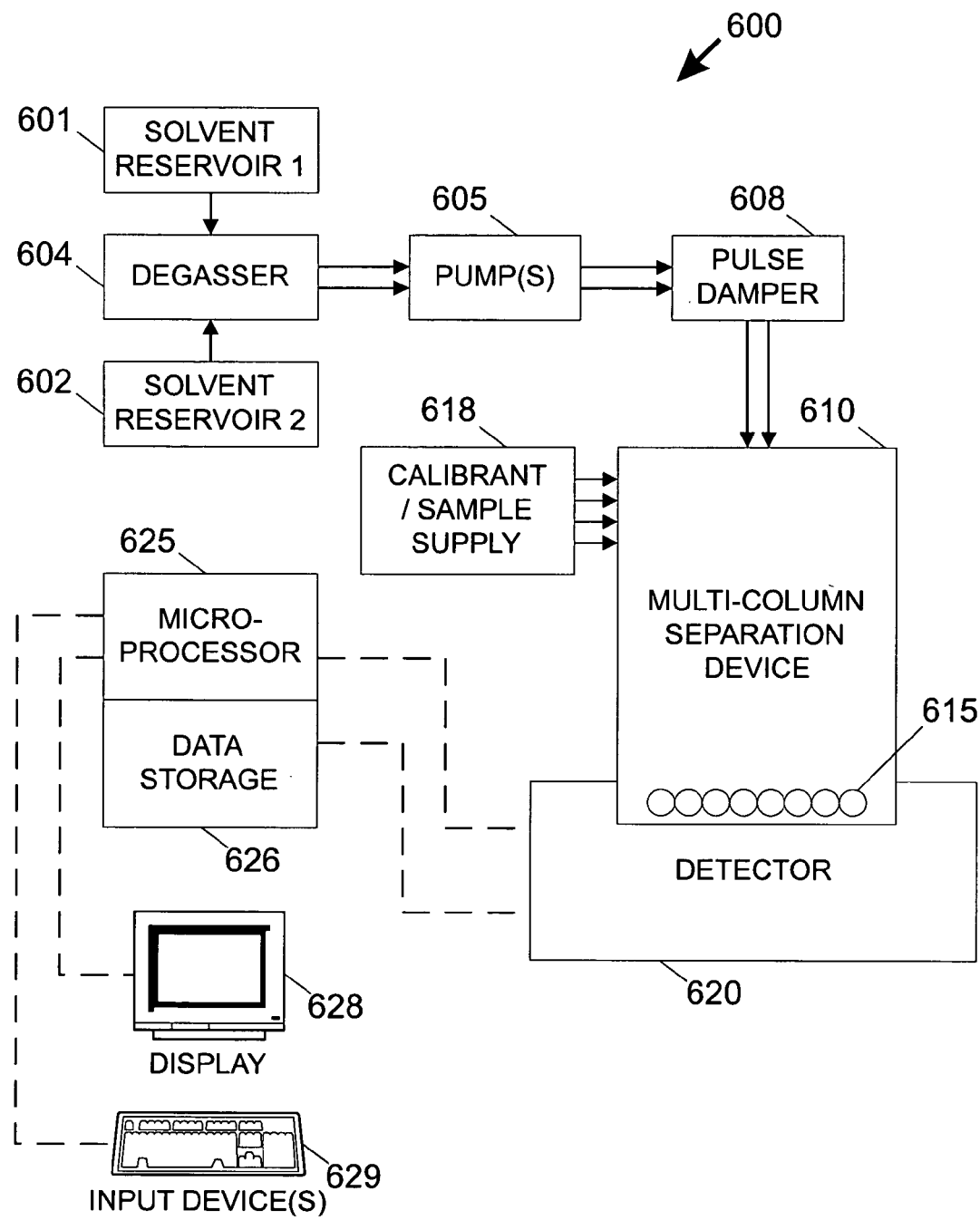
FIG._17

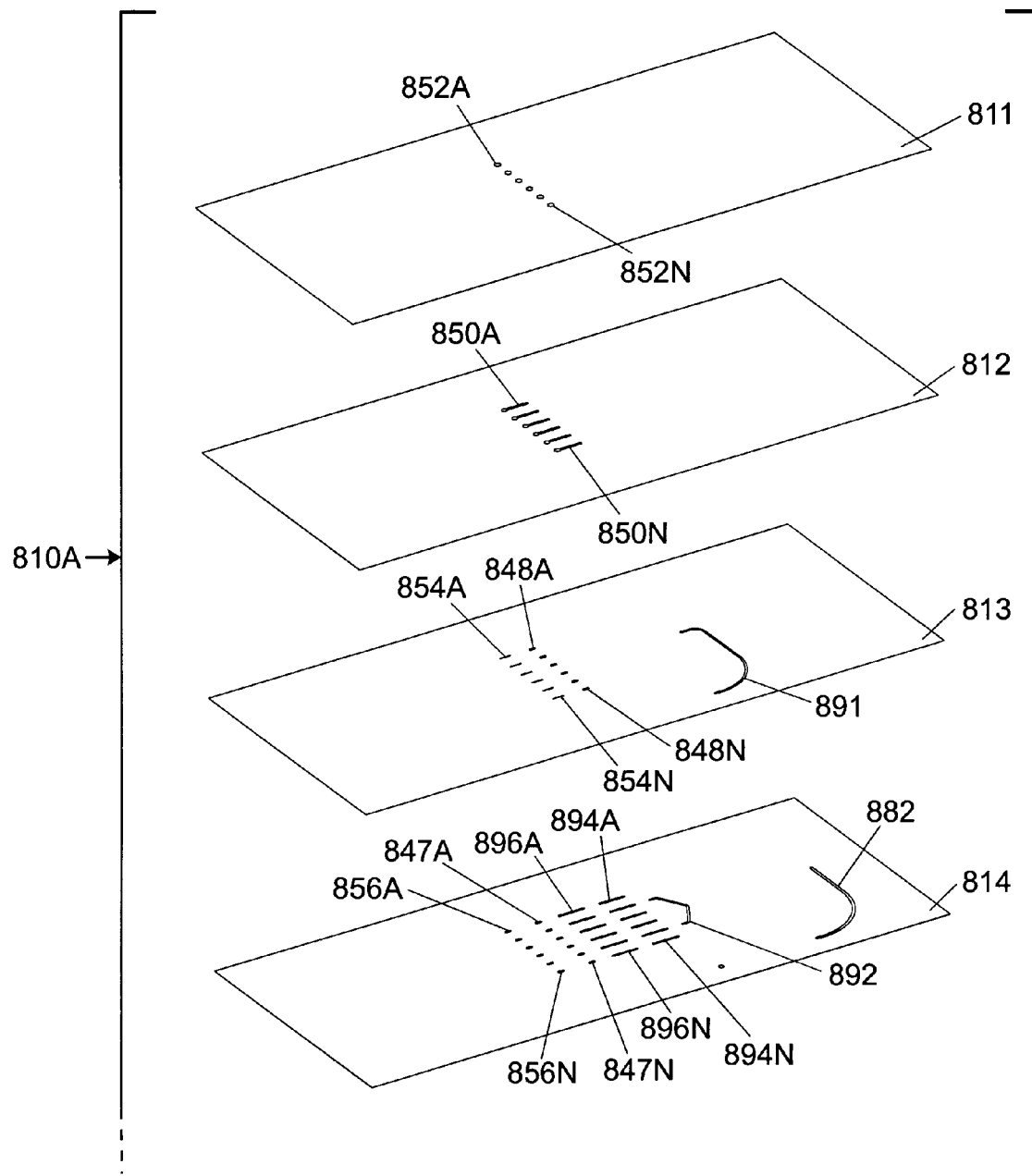
FIG._18A

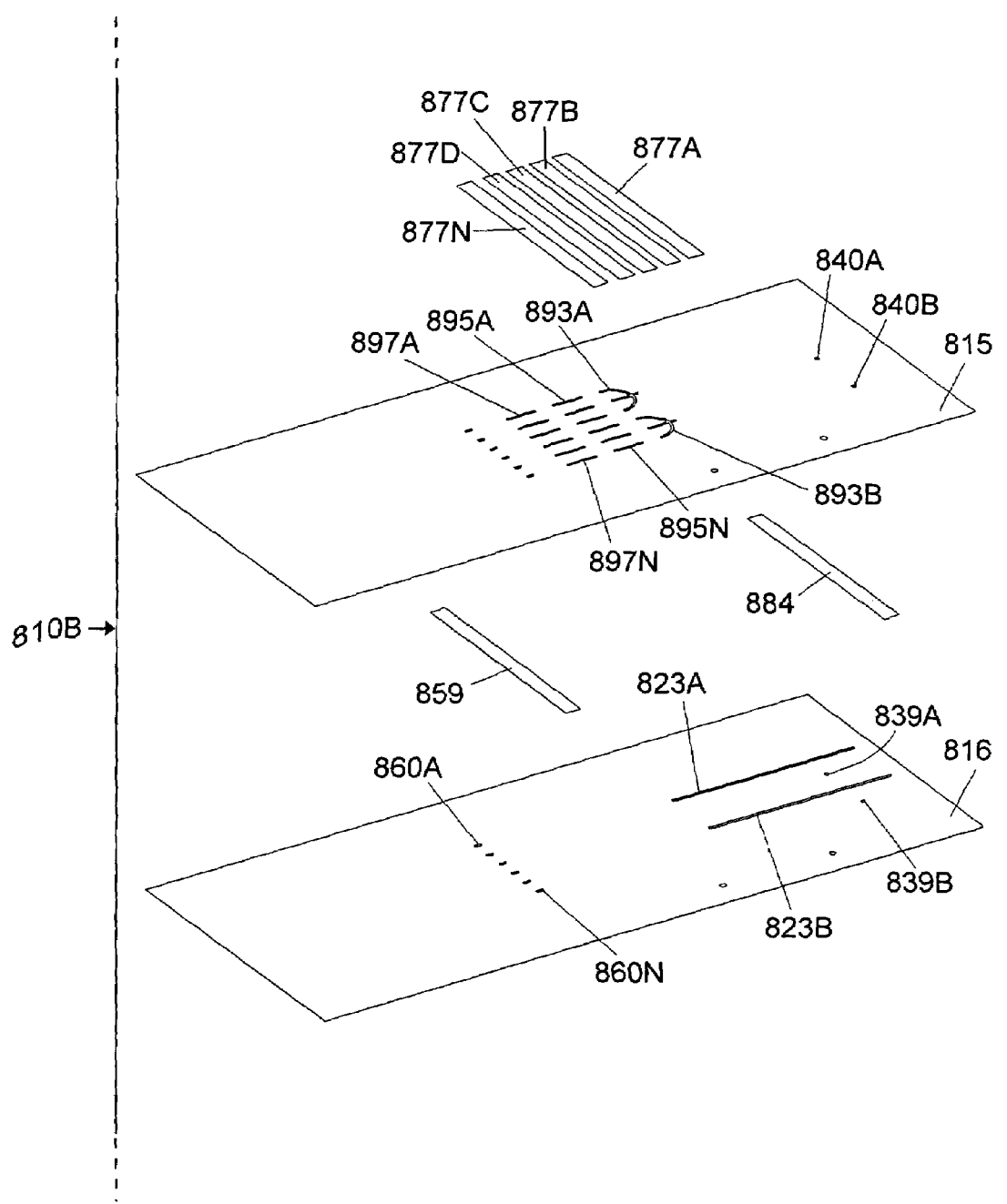
FIG._18B

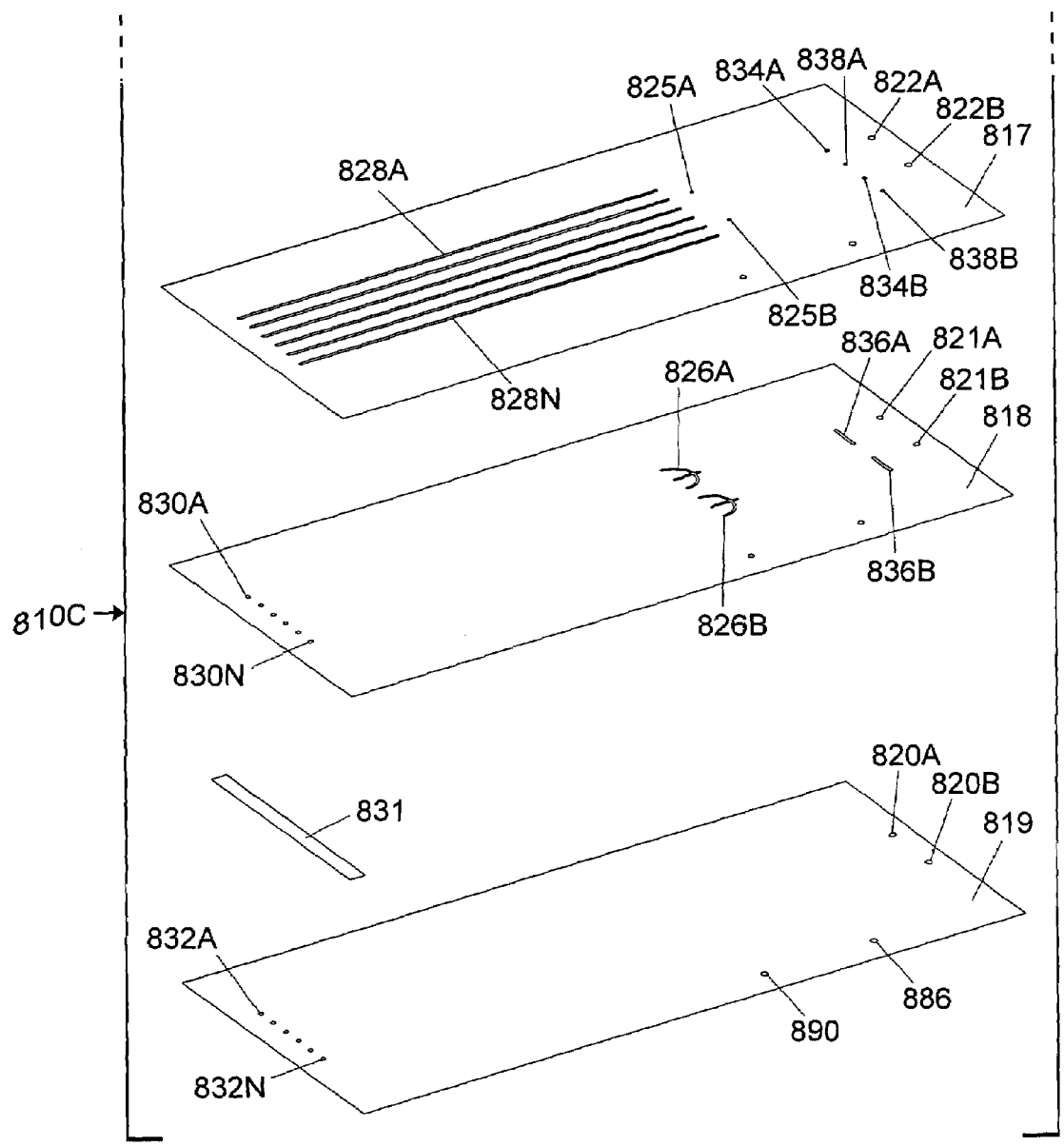
FIG._18C

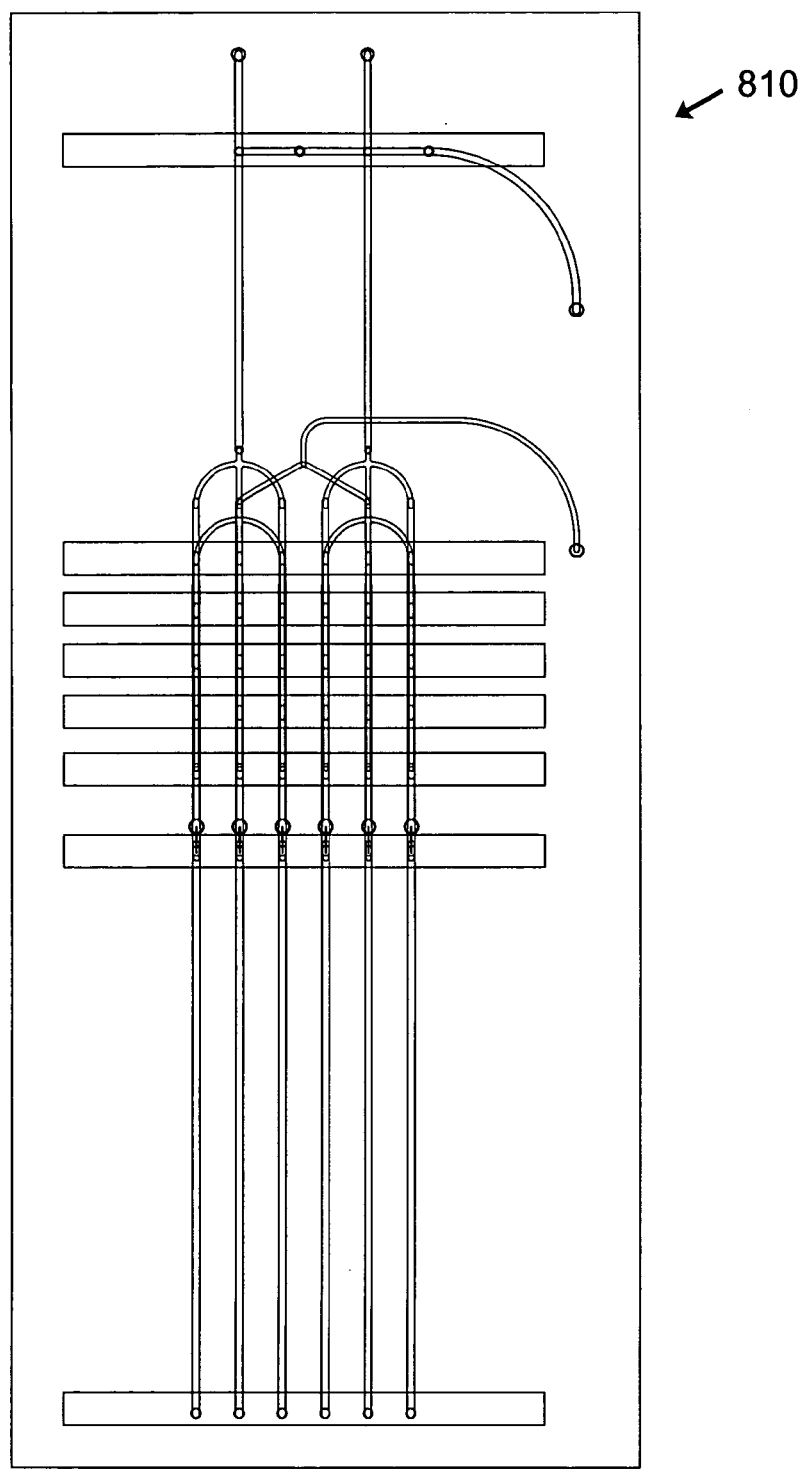
FIG._18E

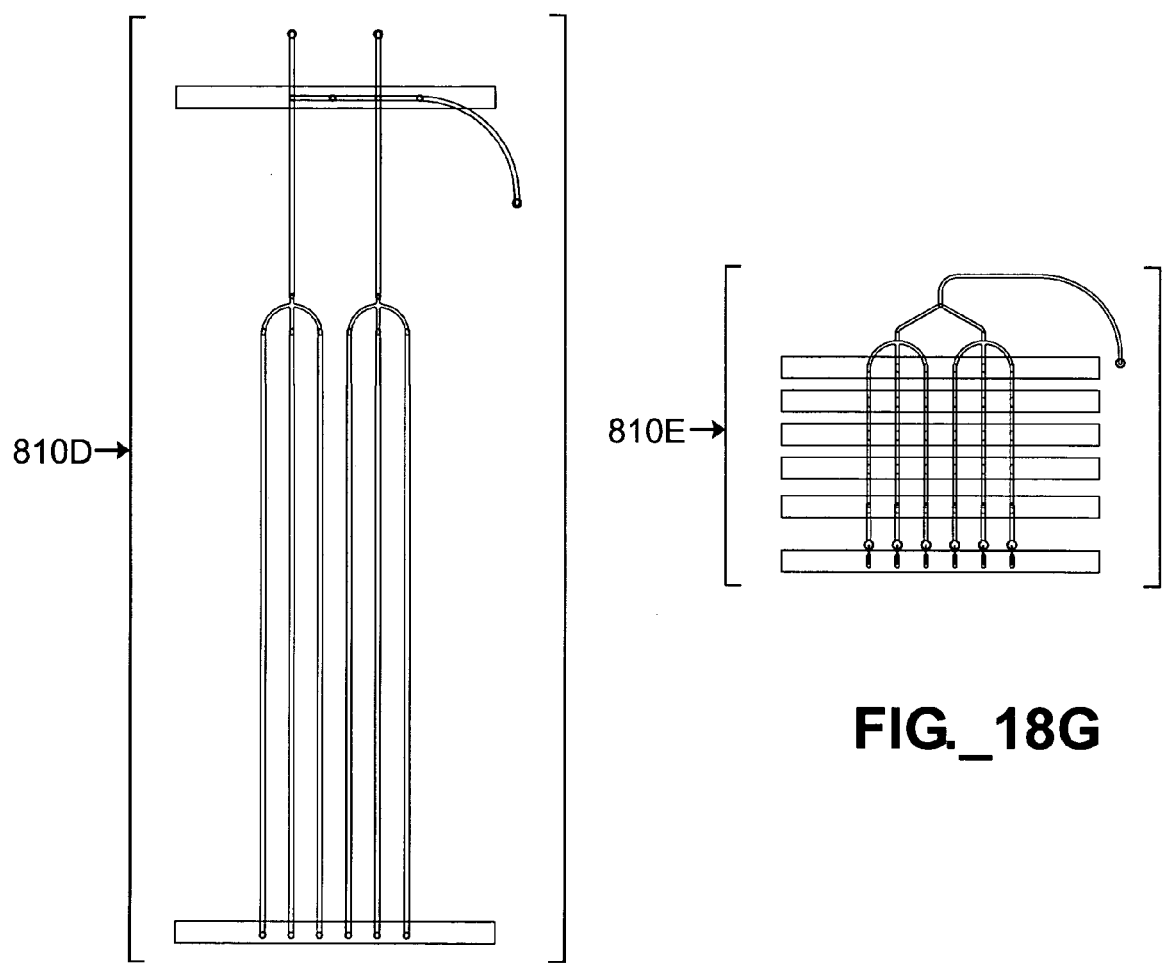
FIG._18F
FIG._18G

_PARALLEL FLUID PROCESSING SYSTEMS AND METHODS_

STATEMENT OF RELATED APPLICATION(S)

This application claims benefit of U.S. provisional patent application Ser. No. 60/461,846 filed Apr. 10, 2003.

FIELD OF THE INVENTION

The present invention relates to fluid processing, such as may be used for synthesizing and/or analyzing various chemical or biological substances.

BACKGROUND OF THE INVENTION

Recent advances in various scientific and industrial fields have dramatically increased the desirability of synthesizing new chemical and biological substances, and have similarly increased the need to analyze these substances, e.g., to identify their active components, verify their stability, and optimize processes for their manufacture. In an effort to accelerate these capabilities, researchers have sought to introduce a higher degree of automation to synthetic and analytical processes as well as increase the number of processes performed in parallel. Most of these processes are performed with fluids (e.g., liquids and/or gases).

To increase the efficiency of fluid processing performed in parallel, it would be desirable to reduce the number of expensive fluid supply components, such as pumps, valves, regulators, and pulse dampers. Providing common fluid supply components and fluidic splitting networks for supplying common fluid(s) to multiple process regions would appear to address such efficiency concerns. If common fluid supply components are used for parallel fluid processing systems, however, another concern is ensuring that each process region is subject to reproducible process conditions. For example, if it is desired to evenly split common supplies of solvents or reagents to multiple process regions, it may be difficult to ensure that each process region receives a substantially equal flow. The problem may be exacerbated by the presence of solid materials, such as catalysts or separation media, e.g., due to variations in solid particle types, sizes, and/or packing density. Additional concerns may arise if it is desired to vary the composition of common solvents or reagents over time, since it can be difficult to ensure that each process region is subject to the same supply fluid composition at substantially the same time. While instrumentation and flow control devices might be added to each process region to address these problems, adding such components can rapidly increase the complexity and cost of parallel fluid processing systems to the point that they are no longer economical to build, operate, or maintain. Moreover, if microfluidic process regions are used, it can be difficult to accurately measure extremely low fluid flow rates supplied to individual process regions.

In the absence of systems or methods for ensuring that reproducible process conditions are maintained in parallel fluid processing systems, it can be difficult to draw confident conclusions from data obtained from individual process regions in different experimental runs, let alone compare data obtained from multiple process regions in the same experimental run. As a result, the scientific utility of efficient parallel fluid processing systems appears to be limited.

The following example is provided to illustrate one type of fluid processing system and issues associated therewith.

One useful analytical process called "chromatography" is routinely performed in various industrial and academic settings. Chromatography encompasses a number of methods for separating various components of mixtures. Liquid chromatography ("LC") is a physical method of separation wherein a liquid "mobile phase" (typically consisting of one or more solvents) carries a sample containing multiple constituents or species through a separation medium or "stationary phase." Various types of mobile phases and stationary phases may be used. Stationary phase material typically includes a solid material disposed within a tube or other boundary. To provide increased surface area so as to enhance separation efficiency, the solid material may be in the form of packed granules (particulate material). The packed material contained by the tube or similar boundary is commonly referred to as a "separation column." High pressure is often used to obtain a close-packed column with minimal voids between adjacent particles, since better resolution during use is typically obtained from more tightly packed columns. As an alternative to packed particulate material, a porous monolith or similar matrix may be used. So-called "high performance liquid chromatography" ("HPLC") refers to efficient separation methods that are typically performed at high operating pressures.

Typical interactions between stationary phases and solutes include adsorption, ion-exchange, partitioning, and size exclusion. Commonly employed stationary phase base materials include silica, alumina, zirconium, or polymeric materials. A stationary phase material may act as a sieve to perform simple size exclusion chromatography, or the stationary phase may include functional groups (e.g., chemical groups) to perform other (e.g., adsorption or ion exchange separation) techniques.

Mobile phase is forced through the stationary phase using means such as one or more pumps, voltage-driven electrokinetic flow, gravitational force, or other established means for generating a pressure differential. After sample is injected into the mobile phase, such as with a conventional loop valve, components of the sample will migrate according to interactions with the stationary phase and the flow of such components are retarded to varying degrees. Individual sample components may reside for some time in the stationary phase (where their velocity is essentially zero) until conditions (e.g., a change in concentration of a mobile phase solvent) permit a component to emerge from the column with the mobile phase. In other words, as the sample travels through voids or pores in the stationary phase, the sample may be Separated into its constituent species due to the attraction of the species to the stationary phase. This attraction may be overcome due to, for example, a change in mobile phase composition. The time a particular constituent spends in the stationary phase relative to the fraction of time it spends in the mobile phase will determine its velocity through the column. Following separation in an LC column, the eluate stream contains series of regions having an elevated concentration of individual component species, which can be detected by various detection techniques to identify and/or quantify the species As illustrated in FIG. 1, a separation column for use in a conventional hydrostatic pressure-driven chromatography system is typically fabricated by packing particulate material 14 into a tubular column body 12. A conventional column body 12 has a high precision internal bore 13 and is usually manufactured with stainless steel, although materials such as glass, fused silica, and/or PEEK are also used. Various methods for packing a column body may be employed. In one example, a simple packing method involves dry-packing an empty tube by shaking particles downward with the aid of vibration from a sonicator bath or an engraving tool. A cut-back pipette tip may be used as a particulate reservoir at the top (second end), and the tube to be packed is plugged with parafilm or a tube cap at the bottom (first end). Following dry packing, the plug is removed and the tube 10 is then secured at the first end with a ferrule 16A, a fine porous stainless steel fritted filter disc (or "frit") 18, a male end fitting 20A, and a female nut 22A that engages the end fitting 20A. Corresponding connectors (namely, a ferrule 16B, a male end fitting 20B, and a female nut 22B) except for the frit 18 are engaged to the second end to secure the dry-packed tube 12. The contents 14 of the tube 12 may be further compressed by flowing pressurized solvent through the packing material 14 from the second end toward the first (frit-containing) end. When compacting of the particle bed has ceased and the fluid pressure has stabilized, there typically remains some portion of the tube 13 that does not contain densely packed particulate material. To eliminate the presence of a void in the column 10, the tube 13 is typically cut down to the bed surface (or a shorter desired length) to ensure that the resulting length of the entire tube 12 contains packed particulate 14, and the unpacked tube section is discarded. Thereafter, the column 10 is reassembled (i.e., with the ferrule 16B, male end fitting 20B, and female nut 22B affixed to the second end) before use.

A conventional pressure-driven liquid chromatography system utilizing a column 10 is illustrated in FIG. 2. The system 30 includes a solvent reservoir 32, at least one (preferably two) high pressure pump(s) 34, a pulse damper 36, a sample injection valve 38, and a sample source 40 all located upstream of the column 10, and further includes a detector 42 and a waste reservoir 44 located downstream of the column 10. The high pressure pump(s) 34 pressurize mobile phase solvent from the reservoir 32. A pulse damper 36 serves to reduce pressure pulses caused by the pump(s) 34. The sample injection valve 38 is typically a rotary valve having an internal sample loop for injecting a predetermined volume of sample from the sample source 40 into the solvent stream. Downstream of the sample injection valve 38, the column 10 contains stationary phase material that aids in separating species of the sample. Downstream of the column 10 is a detector 42 for detecting the separated species, and a waste reservoir 44 for ultimately collecting the mobile phase and sample products. A backpressure regulator (not shown) may be disposed between the column 10 and the detector 42. Many components of the system 30 are precision manufactured, thus elevating the cost of a typical high performance liquid chromatography system 30 to approximately $20,000–$30,000 or more. Owing to the ever-increasing demand for chromatographic separations, once such a system 30 is purchased, it is often operated on a nearly continuous basis.

The system 30 generally permits one sample to be separated at a time in the column 10. Due to the cost of conventional tubular chromatography columns, they are often re-used for many (e.g., typically about one hundred or more) separations. Following one separation, the column 10 may be flushed with a pressurized solvent stream in an attempt to remove any sample components still contained in the stationary phase material 14. However, this time-consuming flushing or cleaning step does not always yield a completely clean column 10. This means that, after the first separation performed on a particular column, every subsequent separation may potentially include false results due to contaminants left behind on the column from a previous run. Eventually, columns become fouled to the point that they are no longer useful, at which point they are removed from service. A spent column is removed from the system 30 by disengaging threaded fittings, and a new column 30 must be carefully connected via the same threaded fittings to prevent unintended leakage.

To provide increased throughput without concomitantly increased cost, a conventional chromatography system may be modified to split the flow from a common set of one or more (typically two) high pressure pumps to several chromatography columns. Such a system 50 is illustrated in FIG. 3. Mobile phase solvent from a solvent reservoir 52 is pressurized by one or more common high pressure pumps 54, and pressure variations caused by the common pump(s) 54 are damped by a common pulse damper 56. Downstream of the pulse damper 56, the solvent flow is split among multiple columns 10A, 10B, 10N each having an injection valve 58A, 58B, 58N and sample source 60A, 60B, 60N. (Although FIG. 3 shows three columns 10A, 10B, 10N, it will be readily apparent that any number of columns 10A, 10B, 10N may be provided. For this reason, the designation "N" is used to represent the last column 10N, with the understanding that "N" represents a variable and could represent any desired number of columns.) Downstream of each column 10A, 10B, 10N is a detector 62A, 62B, 62N and a waste reservoir 64A, 64B, 64N.

Compared to the system 30 described in connection with FIG. 2, the enhanced system 50 permits significantly higher throughput, since several samples can be analyzed in parallel. Additionally, in the system 50, this increased throughput comes at a lower cost per column/analysis, since the cost of expensive solvent delivery components (particularly the high pressure pumps 54 and pulse damper 56) is spread over multiple columns 10A, 10B, 10N. That is, a single parallel chromatography system 50 having common solvent delivery components and several (i.e., "N") separation columns is substantially less expensive than a comparable ("N") number of chromatography systems each having discrete solvent delivery components.

One alternative to using multiple discrete columns 10A, 10B, 10N in the system 50 is to utilize a microfluidic separation device having multiple separation columns that permit multiple chromatographic separations to be conducted in parallel, such as the device 100 illustrated in FIGS. 4A–4B. Preferably, such a device 100 contains multiple (e.g., eight) columns 145A–145X and is substantially planar to permit easy interface with one or more flat gasketed surfaces (not shown) for mating with solvent delivery components, detectors, and other desirable operational elements. This permits the device 100 to be interchanged rapidly as compared to the use of tubular columns (e.g., columns 10A, 10B, 10N) having conventional threaded fittings. Yet another device 400 having twenty-four separation columns 439A–439X permitting even higher throughput is illustrated in FIG. 5 and FIGS. 6A–6E. Further details regarding these microfluidic separation devices 100, 400 are provided herein.

While using common solvent delivery components with multiple separation columns (e.g., either discrete conventional columns 10A, 10B, 10N or multiple columns 145A–145X, 439A–439X integrated within a unitary device 100, 400) provides certain cost advantages, it also presents new issues compared to the use of single-column systems such as the chromatography system 30 illustrated in FIG. 2. One issue is accounting for different rates of fluid flow through each column in a multi-column system, particularly in low-flow environments not well-suited for inferential flow measurement. Generally, precision pumps used with liquid chromatography systems are of the positive displacement variety, and—assuming negligible leakage of the pump seals—such pumps permit liquid flow to be calculated by multiplying the number of pump strokes in a given period by the volume displaced by each stroke. When a positive displacement pump is coupled to a single column (e.g., a column 10 in the system 30 illustrated in FIG. 2), the rate of fluid flow through the column 10 is simply equal to the output of the pump.

When a common pump supplies multiple columns (e.g., columns 10A, 10B, 10N, 145A–145X, or 439A–439X), however, it is difficult to predict the flow through each individual column—even if the columns appear substantially identical—since impedance to fluid flow varies somewhat from one column to another and fluid flow will be biased toward the column(s) with the least fluidic impedance. That is, even when columns are carefully selected in an attempt to match their impedances, variations between columns will inevitably cause backpressure differences that in turn cause flow rate differences between fluid streams. Such flow variations may be caused by imperfect operation of any flow splitter(s) disposed upstream of the multiple columns, as well as by slight differences in column packing density, column geometry, and interfaces with the columns (e.g., threaded fittings within a chromatography system employing tubular columns or gasketed surfaces within a system employing substantially planar multi-column microfluidic devices).

To further complicate matters, many commonly employed chromatographic techniques utilize a solvent profile that changes with time. For example, common reverse phase chromatographic techniques use gradient elution wherein two individually controllable pumps supply two different mobile phase fluids (e.g., water and an organic solvent) that are mixed upstream of the separation column. (Contrast isocratic elution in which the solvent concentration remains constant so only a single pump is needed). Typically, separations in reverse phase chromatography depend on the reversible adsorption/desorption of solute molecules with varying degrees of hydrophobicity to a hydrophobic stationary phase. Thus, in a parallel multi-column system employing a common set of pumps for performing gradient elution, the presence of a changing solvent concentration exacerbates the difficulty of ensuring that identical mobile phase conditions (i.e., including both flow rate and concentration) are provided to each column at the same time.

Yet another potential source of variability in common-fluid-supply parallel HPLC systems employing low-pressure injection may be caused by the application of a pressure ramp to the columns following sample injection. Conventional HPLC systems, which use a loop injection valve for supplying sample to a column, permit sample introduction without depressurizing the column. In certain other systems, such as the planar multi-column systems described below, however, samples may be injected onto columns at low pressure (e.g., atmospheric pressure), followed by a pressure ramp up to a desirable operating pressure. Pressure ramps are inherently transient conditions, and can lead to unpredictable flow patterns in a common-fluid-supply parallel separation system before steady-state flow conditions are attained. These unpredictable flow patterns exacerbate column-to-column variability Due to the difficulty of providing identical mobile phase conditions to each column in a parallel separation system with a common fluid supply, seemingly identical columns tend to perform differently. That is, if an identical sample mixture is provided to multiple columns in a common-fluid-supply parallel separation system with common mobile phase supply pumps for providing gradient conditions, individual species exhibit different retention times from one column to another. These different retention times are not merely proportional to flow. Applicants have confirmed this proposition experimentally by adding an unretained component (species that does not interact with the stationary phase and can be detected downstream to infer flow rate through a column) to the sample and simply correcting the retention times of unretained peaks. The simple phase shift based on flow rate did not yield nearly identical retention times from one column to another. As a result of the different performance characteristics of seemingly identical columns in a parallel separation system with a common fluid supply, it is difficult to compare analytical results obtained from one column to another.

The output of a chromatographic separation is a plot called a chromatogram, which is a graphical or other representation of the response of a detector to a property of the effluent versus time. For example, if UV-visible ("UV-VIS") detection is used, then a chromatogram may include a plot of absorbance units versus time. An example of such a chromatogram resulting from separation of mixture of uracil and four parabens (methyl, ethyl, propyl, and butyl) (hereinafter, "Applicant's standard test mixture") is provided in FIG. 7. Each of the components interacts differently with the stationary phase material (uracil does not interact at all), and therefore each has a different retention time (i.e., time corresponding to each peak in the chromatogram). More specifically, the retention time for a particular species is the time required for the species (initially contained in a sample) to travel from the injection port through the column to the detector. Retention times are used to identify components (species) in a particular sample. Due to the variation in performance among different separation columns, however, the retention time of a particular species in a sample eluted in a first column may be different from the retention time of the same species in the same sample eluted in a second column seemingly identical to the first. This is evident, for example, in FIG. 8, which provides superimposed chromatograms obtained using the same sample in multiple separation columns having a common mobile phase supply operated in gradient mode; although three species were eluted in each column, their retention times vary significantly. As evident from FIG. 9, in which the individual chromatograms from FIG. 8 have been time-shifted to a common retention time for the first unretained peak, a mere phase shift is generally insufficient to eliminate column-to-column variability for the remaining (retained) species. Since retention times are used to identify species within a sample, variation in retention times from one column to another increases the uncertainty of positively identifying individual species. It would be desirable to reduce this uncertainty; i.e., to provide an increased ability to discriminate between species with similar retention times, no matter which column in a common-fluid-supply parallel separation system is used.

There exist further reasons why it would be desirable to permit comparison between the outputs of different process regions (e.g., columns) in a parallel fluid processing system with a common fluidic input split among the process regions. One reason such comparison would be desirable is to enable the identification of "bad" experimental data, particularly those caused by difficulties with a particular process region. Conventionally, determining whether a particular process region is not working properly requires a skilled technician to compare and analyze data obtained using the same sample or reagent from multiple different process regions.

While certain performance variations among different process regions may be is relatively normal (e.g., different retention times among different separation columns in a multi-column system), the presence of more substantial differences (e.g., in chromatography, factors including peak shape and peak amplitude) can lead to a determination that a particular separation column is not functioning properly. It would be desirable to provide a process region evaluation method that could be automated, to not only reduce the time and skill required to evaluate process regions, but also rapidly validate experimental data.

In view of the foregoing, there exists a need for systems and methods for enhancing the utility of parallel fluid processing systems.

BRIEF DESCRIPTION OF THE DRAWINGS

FIG. 1 is a cross-sectional view of a conventional tube-based separation column for performing pressure-driven liquid chromatography.

FIG. 2 is a schematic of a conventional liquid chromatography system employing the separation column of FIG. 1.

FIG. 3 is a schematic of a conventional multi-column liquid chromatography system employing a common fluid supply and multiple tubular separation columns according to the column of FIG. 1.

FIG. 4B is a top view of the assembled device of FIG. 4A.

FIG. 6A is an exploded perspective view of a first portion, including the first through fourth layers, of the device shown in FIG. 5.

FIG. 6B is an exploded perspective view of a second portion, including the fifth and sixth layers, of the device shown in FIG. 5.

FIG. 6E is a reduced scale composite of FIGS. 6A–6D showing an exploded perspective view of the device of FIG. 5.

FIG. 7 is an uncorrected chromatogram (absorbance units versus time) obtained from the separation of a mixture of uracil and four parabens (methyl, ethyl, propyl, and butyl) (hereinafter, "Applicants' standard test mixture") in a single separation column.

FIG. 8 is an uncorrected superimposed chromatogram (absorbance units versus time) obtained from the separation of Applicants' standard test mixture in three parallel separation columns in fluid communication with a common fluid supply.

FIG. 9 is a superimposed, phase-shifted chromatogram (absorbance units versus time) obtained from the separation of Applicants' standard test mixture in three parallel separation columns in fluid communication with a common fluid supply, the results from each column including a phase shift to a common retention time for the first (unretained) component.

FIG. 10 is a superimposed raw chromatogram (absorbance units versus time) obtained from the separation of Applicants' standard test mixture in twenty-four parallel separation columns in fluid communication with a common fluid supply.

FIG. 11 is a superimposed corrected chromatogram (absorbance units versus time) obtained by correcting the retention times of the chromatographic data depicted in FIG. 10.

FIG. 12A is a table providing raw retention times for a first separation of Applicants' standard test mixture in a twenty-four column separation device substantially similar to the device of FIG. 5 and FIGS. 6A–6E, the retention time data corresponding to the corrected chromatogram of FIG. 10.

FIG. 12B is a table of correction factors derived from the data depicted in FIG. 12A.

FIG. 12C is a table providing corrected retention times obtained by applying the correction factors of FIG. 12B to the raw data depicted in FIG. 12A, the resulting corrected retention time data corresponding to the superimposed corrected chromatogram of FIG. 11.

FIG. 12D is a table providing raw retention times for a second separation of Applicants' standard test mixture in a twenty-four column parallel separation device substantially similar to the device of FIG. 5 and FIGS. 6A–6E.

FIG. 12E is a table providing corrected retention times obtained by applying the correction factors of FIG. 12B to the raw data provided in FIG. 12D for the second separation of Applicants' standard test mixture in a twenty-four column parallel separation device.

FIG. 13 is a flowchart of a method for correcting fluid process data obtained from multiple process regions in fluid communication with a common fluid source.

FIG. 14 is flowchart of a method for correct retention times for a multi-column parallel liquid chromatography system with the columns in fluid communication with a common supply of mobile phase by way of a splitting network.

FIG. 15A is a table including peak areas and correction factors obtained from a first (calibration) run using Applicant's standard test mixture in each column of a twenty-four column parallel separation device substantially similar to the device of FIG. 5 and FIGS. 6A–6E.

FIG. 15B is a table including raw and corrected peak areas for the third peak (peak 3) of each column for a second run of the same parallel separation device as used in connection with FIG. 15A, with the peak area corrections performed with the correction factors derived from the data provided in FIG. 15A.

FIG. 16A is a plot of raw third peak area versus column number for the raw third peak (peak 3) data provided in FIG. 15A.

FIG. 16B is a plot of corrected third peak area versus column number for the corrected third peak (peak 3) data provided in FIG. 15B.

FIG. 17 is a schematic of a system for data correction in multi-column liquid chromatography.

FIG. 18A is an exploded perspective view of a first portion, including the first through fourth layers, of a parallel fluid processing device having two parallel groups of three fluid process regions, with each group of process regions having a separate solid distribution network, and both groups of fluid process regions being in fluid communication with a common splitting network permitting fluid communication with a common fluid supply.

FIG. 18B is an exploded perspective view of a second portion, including the fifth and sixth layers, of the parallel fluid processing device of FIG. 18A.

FIG. 18C is an exploded perspective view of a third portion, including the sixth through ninth layers, of the parallel fluid processing device of FIG. 18A.

FIG. 18E is a top view of the assembled device of FIGS. 18A–18D.

FIG. 18F is a top view of a first portion of the device of FIGS. 18A–18E illustrating two distinct slurry distribution networks and six process regions.

FIG. 18G is a top view of a second portion of the device of FIGS. 18A–18E illustrating a common fluid supply network.

DETAILED DESCRIPTION OF PREFERRED EMBODIMENTS

Definitions

Figure 4A:
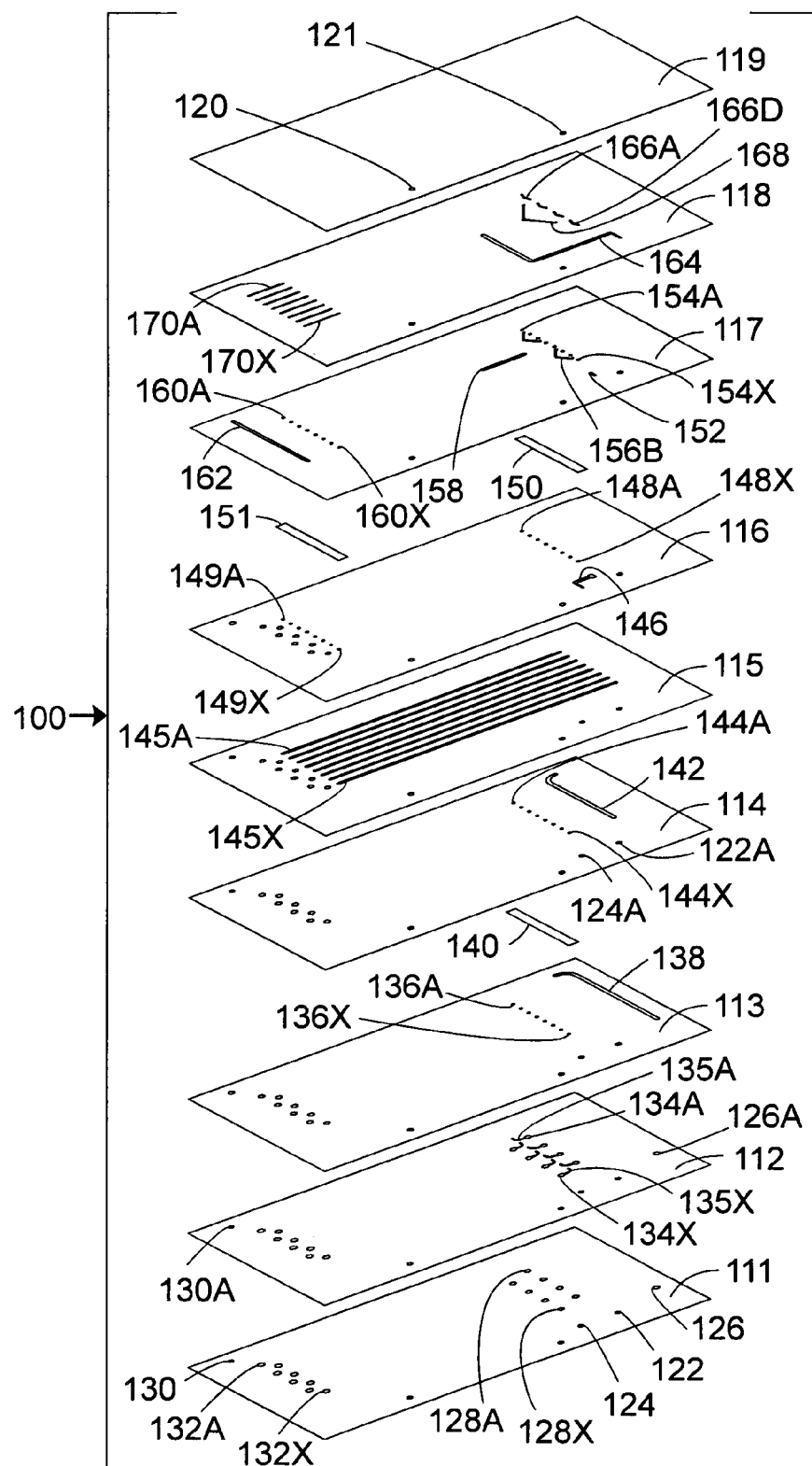
FIG. 4A is an exploded perspective view of a first multi-layer microfluidic chromatographic separation device including eight microfluidic separation columns and a splitting network permitting fluid communication with a common mobile phase supply.
Figure 5:
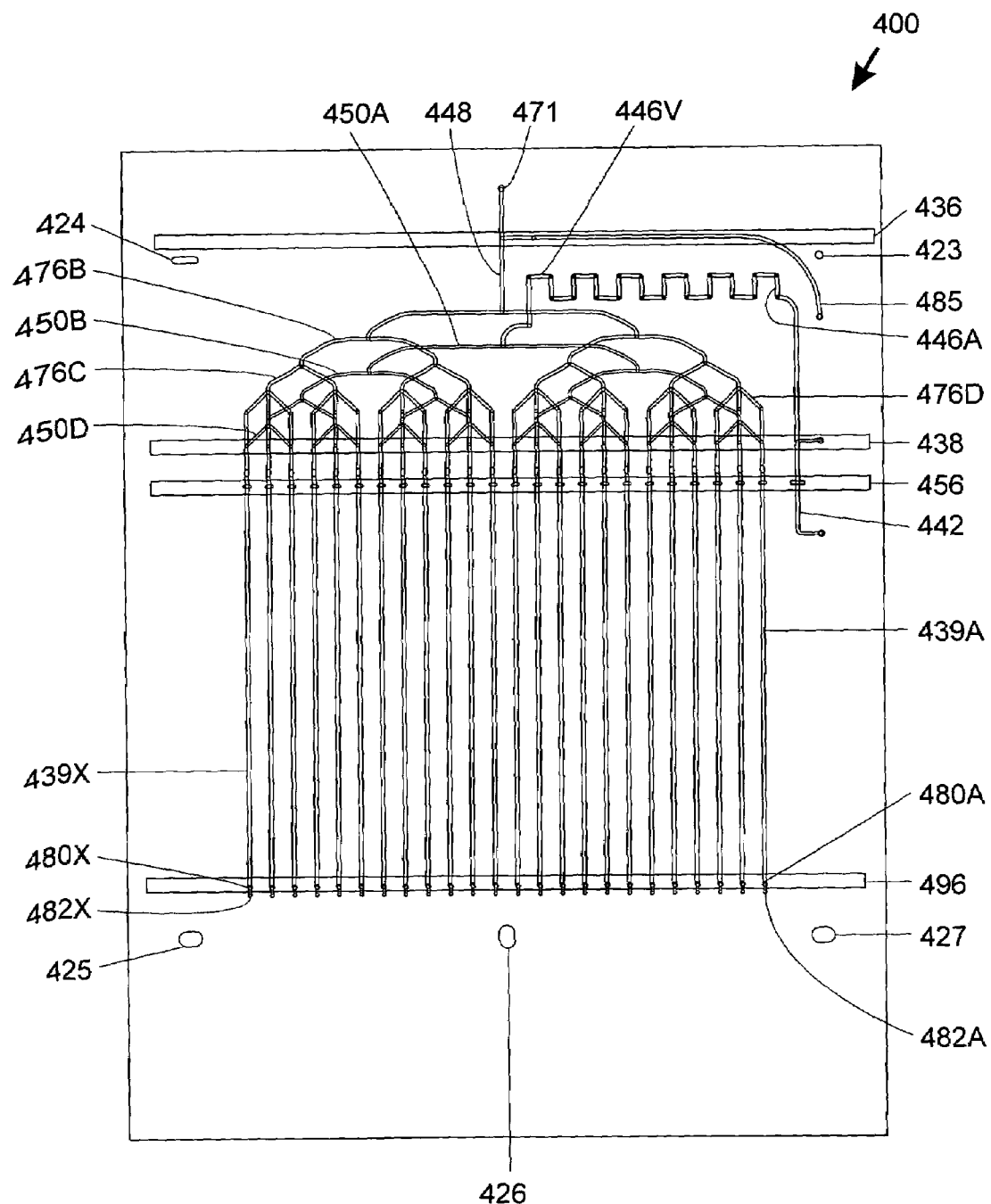
FIG. 5 is a top view of a second multi-layer microfluidic liquid chromatographic separation device including a splitting network permitting fluid communication with a common mobile phase supply.

The term "analysis" refers to the separation, extraction, purification, and/or identification of one or more ingredients of a substance.

The terms "channel" or "chamber" as used herein are not intended to be restricted to elongated configurations where the transverse or longitudinal dimension greatly exceeds the diameter or cross-sectional dimension. Rather, such terms are meant to comprise cavities or tunnels of any desired shape or configuration through which liquids may be directed. Such a fluid cavity may, for example, comprise a flow-through cell where fluid is to be continually passed or, alternatively, a chamber for holding a specified, discrete amount of fluid for a specified amount of time. "Channels" and "chambers" may be filled or may contain internal structures comprising, for example, valves, filters, and similar or equivalent components and materials.

The terms "chromatography column" and "column" are used interchangeably herein and refer to a device or portion thereof comprising stationary phase material that is capable of separating at least a portion of an analyte in a fluid.

The term "fluid process" as used herein refers to a series of actions or operations utilizing a fluid, characterized by any analysis and/or synthesis.

The term "fluid process region" as used herein refers to a region adapted to perform a fluid process.

The term "microfluidic" as used herein is to be understood to refer to structures or devices through which fluid(s) are capable of being passed or directed, wherein one or more of the dimensions is less than 500 microns.

The term "microfluidic system" as used herein refers to a microfluidic path, often including one or more microfluidic devices, capable of carrying or holding fluids. A microfluidic system may be composed of one or more subsystems.

The term "parallel" as used herein refers to the ability to concomitantly or substantially concurrently process two or more separate fluid volumes, and does not necessarily refer to a specific channel or chamber structure or layout.

The term "substantially sealed" as used herein refers to the condition of having a sufficiently low unintended leakage rate and/or leakage volume under given flow, fluid identity, or pressure conditions. Types of unintended leakage include leakage or pooling that accumulates in unintended regions between device layers and leakage to an environment outside a microfluidic device. A substantially sealed microstructure is contemplated to have one or more fluidic ports or apertures to provide desirable fluidic inlet or outlet utility.

The term "stencil" as used herein refers to a preferably substantially planar material layer or sheet through which one or more variously shaped and oriented portions have been cut or removed through the entire thickness of the layer, and which removed portions permit substantial fluid movement within the layer (as opposed to simple throughholes or vias for transmitting fluid from one layer to another layer). The outlines of cut or removed portions form the lateral boundaries of microstructures that are formed when a stencil is sandwiched between other layers, such as substrates or other stencils.

The term "synthesis" as used herein refers to molecular rearrangement, addition, or subtraction of molecular species, generally including either chemical or biological transformation. Biological transformations include bioanalytical methods for the detection and quantification of molecular species of interest, also referred to herein as bioassays or assays.

Parallel Fluid Processing Generally

Various types of fluid processing are contemplated by the present invention. As noted previously, the term "fluid process" refers to a series of actions or operations utilizing a fluid, characterized by analysis and/or synthesis. A non-exhaustive list of examples of broad types of fluid processing includes: chromatography, electrophoresis, specific- and non-specific binding studies, chemical and biological assays, and synthesis and/or screening of production of peptides, proteins, and DNA and RNA oligomers. Classes of chemical synthesis processes that may be performed include (1) Amide bond forming reactions (such as formation of sulfonamide, guanidine, phosphoramide, thiourea, urea, and urethane, and amine acylation); (2) Aromatic substitution reactions (such as aryl—aryl coupling, Friedel-Crafts acylation and alkylation, nucleophilic substitution, and metal-promoted coupling); (3) Condensation reactions (such as formation of acetal, enamine, and imine, and Aldol and Claisen condensation and variations thereof); (4) Cycloaddition reactions (such as [2+2] cycloaddition, Diels-Alder, and 1,3-Dipolar addition); (5) Polar addition and elimination reactions (such as Grignard reactions, Michael addition, hydration, halogenation, and dehydration); (6) Heterocycle forming reactions (such as formation of benzimidazole, hydantoin, piperidine, imidazole, indole, iosxazole, lactam, and pyrazole); (7) Olefin forming reactions (such as elimination, Wittig and related reactions); (8) oxidation reactions (such as those involving the use of transition metal oxidants, PCC, peroxide, and oxidations using oxygen/air/ozone/nitric acid); (9) Reduction reactions (such as dissolving metal, catalytic hydrogenation, and metal hydride); and (10) other reactions and processes including enzymatic resolutions, asymmetric synthesis and resolution using chiral templates or catalysts, and other reactions using functional group manipulation as applied to multi-step synthesis. Additionally, biochemical and electrophysiological assays may be performed, including: (1) genomic analysis (sequencing, hybridization), PCR and/or other detection and amplification schemes for DNA, and RNA oligomers; (2) gene expression; (3) enzymatic activity assays; (4) receptor binding assays; and (5) ELISA assays. The foregoing assays may be performed in a variety of formats, such as: homogeneous, bead-based, and surface bound formats including microtiter-based assays using any of a number of detection schemes known to those skilled in the art. Further contemplated are biological reactions such as elucidation, prediction and manipulation of metabolic pathways in an organism under study using traditional tools, continuous production of biomolecules using specified enzymes or catalysts, and production and delivery of biomolecules or molecules active in biological systems, such as a therapeutic agents.

Preferably, fluid process regions are adapted for flow-through fluid processing. That is, rather than providing fluid processing utility in a static environment, during a fluid processing step at least one fluid preferably flows substantially continuously through each fluid process region, although fluid flow rates through individual process regions may be low or extremely low if desired. Flow-through fluid processing can be used to promote fluid mixing without the need for stirring mechanisms or other active mixing means. Fluid mixing is particularly aided by fluid flow if a fluid process region contains a packed bed or porous medium. Overlap mixers (such as described in commonly assigned U.S. Pat. No. 6,935,772) or other conventional passive mixing means may be used.

In certain embodiments, fluid process regions contain solid materials. Solid materials of various types and functionalities, including separation media and catalyst materials, may be provided. The solid materials contained in different fluid process regions may be substantially the same or substantially different. Solid materials may be coated on the interior walls of a process region using any of various material deposition techniques. In certain embodiments, solid materials include filter materials. In further embodiments, the solids include packed particulate material. If packed particulate materials are used, then a porous retaining material, such as a microporous membrane, is preferably associated with each fluid process region to retain the packed particulate in place, such that the packed particulate material has an average particle size, the porous material has an average pore size, and the average particle size is greater than the average pore size. Such a configuration may be used to trap particulate material within a fluid process region but still permit fluid flow through the fluid process region. A preferred method for packing particulate material within a fluidic process region is to supply the particulate mixed with a liquid in the form of a slurry. For example, an organic solvent, such as acetonitrile, may be mixed with silica particles having C-18 functional groups to form a slurry, then the slurry may be supplied to a fluid process region bounded along one end by a microporous retaining membrane, with much of the liquid solvent exiting the fluid process region by flowing through the porous membrane and much of any remaining solvent exiting the fluid process region by evaporation.

Parallel fluid process regions used within in methods and systems according to the present invention are in fluid communication with at least one common fluid source by way of a splitting network. The use of a common fluid source promotes efficiency by minimizing the use of expensive fluid supply components. In one embodiment, multiple fluid process regions are integrated into a single device, which may also include the splitting network. In other embodiments, a splitting network may be separable from the parallel fluid process regions. More precise and repeatable splitting among the parallel fluid process regions may be promoted with elevated flow resistance regions disposed downstream of the splitting network. Elevated flow resistance regions may be disposed upstream and/or downstream of the fluidic process regions. Multiple elevated flow resistance regions may be disposed in series to provide additive flow resistance. If provided, each elevated flow resistance region or series thereof preferably provides a flow resistance that is significantly greater than the flow resistance of its associated fluid process region—preferably at least about two times greater, more preferably at least about four times greater, and even more preferably at least about eight times greater. Preferably, each parallel elevated flow resistance region is characterized by substantially the same characteristic flow resistance. The presence of elevated impedance regions with relatively repeatable flow impedance characteristics (e.g., porous membranes) tends to reduce the effect of variations in flow resistances among the various parallel fluid process regions and thus promote more consistently even splitting of a common fluid input stream among the fluid process regions.

Each fluid process region is in fluid communication with a common first fluid source by way of a splitting network. One fluid or multiple fluids (e.g., a mixture) may be supplied by the first fluid source. Additionally, each fluid process region is preferably in fluid communication with at least one second fluid source, such as, for example a source of different reagents (e.g., for parallel synthesis) or samples (e.g., for parallel analysis). Preferably, each fluid process region is in independent fluid communication with a different second fluid source. Fluid communication between each fluid process region and the (at least one) second fluid source is preferably intermittent. In one example directed to chromatographic separation, multiple fluid process regions containing stationary phase material are in fluid communication with a common supply of mobile phase solvent (i.e., a "first fluid") that may have a composition that changes with time. Each fluid process region is also in fluid communication with a different sample inlet port, such that different samples (i.e., "second fluids") may be separated simultaneously in the fluid process regions. On-column sample injection, such as described in commonly assigned U.S. Patent Publication No. 2002/0187557 entitled "Systems and methods for introducing samples into microfluidic devices", may be used. Samples contained in multi-well microtiter plates may be transferred to second fluid inlets using single- or multi-head pipettors or similar fluid transfer devices.

Microfluidic Systems

While fluidic system of various types and scales are contemplated, in one embodiment parallel fluid processing is performed with microfluidic systems. Microfluidic systems offer numerous benefits compared to systems utilizing (larger) conventional fluid volumes, including reduced sample usage, reduced reagent consumption, reduced disposal quantities, improved reaction response times, and enhanced safety. Challenges commonly associated with microfluidic systems include metering and splitting extremely small fluid volumes accurately and repeatably; minimizing the effects of evaporation; and prototyping and constructing systems at a reasonable cost.

Traditionally, microfluidic devices have been constructed using techniques borrowed from the silicon fabrication industry. For example, photolithography may be used to define channels on a silicon or similar substrate followed by etching to remove material from one surface of the substrate to form channels and other microstructures capable of conveying fluid. A cover layer may be added to the substrate to enclose the device. More recently, additional methods have been developed that allow microfluidic devices to be constructed from plastic, silicone, or other polymeric materials. Micromolding, embossing, and soft lithography are examples of known construction methods.

Another technique for fabricating microfluidic devices utilizes multiple laminated device layers or sheets including one or more stencil layers that define channels and/or other microfluidic structures through the entire thickness (i.e., including top and bottom surfaces) of the stencil layer(s). Various method for defining channels through the entire thickness of a stencil layer include stamping, die cutting, blade cutting, and laser cutting. A stencil layer thus forms the lateral boundaries of a channel extending longitudinally through the stencil layer, with the channel being further bounded from above and below by the lower and upper surfaces, respectively, of adjacent device layers sandwiching the stencil layer. Multiple stencil layers may be provided in a single device to construct complex fluidic flow paths. Completed devices typically include one or more external fluidic ports permitting fluidic access to the device. Examples of stencil fabrication techniques are described, for example, in WIPO Patent Publication No. WO 01/25138 entitled "Modular Microfluidic Devices Comprising Sandwiched Stencils."

Stencil fabrication techniques offer numerous advantages over other techniques for fabricating microfluidic devices. Most non-stencil methods involve complicated, expensive, and time-consuming fabrication micromachining techniques. Notably, forming a groove or channel that penetrates only part way through a substrate (i.e., micromachining) requires multiple processing steps and control of not only the size of surface features, but also their depth. Additionally, micromachining techniques often vary significantly from one type of material to another. In contrast, the basic technique of cutting channels through stencil layers and then laminating device layers into finished devices is relatively constant across many classes of materials. Even more importantly, however, stencil fabrication offers substantial improvements in the ease, speed, and cost by which such devices can be produced. Stencil techniques thus enable rapid prototyping, which is invaluable for validating and optimizing new device designs.

Detection

Various types of detectors may be used with a parallel fluid processing system to detect species separated and/or products synthesized in fluid process regions. Detection may be performed within, adjacent to, or substantially downstream of fluid process regions. Multiple detection regions may be integrated into a single device, possibly the same device containing multiple fluid process regions; alternatively, one or more detection regions may be remotely located relative to the fluid process regions. Preferably, each fluid process region is associated with a different detector or detector channel. In one embodiment, a multi-channel detector is provided with a dedicated channel for each fluid process region. Alternatively, fewer detector channels than fluidic process regions may be provided, and an appropriate multiplexing, sequential sampling, or other fluidic switching scheme may be used to periodically detect products from different fluid process regions.

Quantitative and/or qualitative detection may be used to measure various physical parameters of the contents of (or what was formerly contained within) each fluid process region. Examples of physical parameters subject to measurement include, but are not limited to: flow, pressure, temperature, optical properties (including absorbance, fluorescence, optical scattering, and evaporative light scattering), electrical properties (conductivity, resistance, capacitance), molecular weight, molecular composition, and elemental composition. Physical parameter measurements may be recorded as a function of time; thus, many physical parameters or values derived therefrom may be recorded as profiles or integrated (aggregate) values for each fluid process region (e.g., flow profile, pressure profile, temperature profile, voltage profile, current profile, molecular weight profile, etc.). Various detector types and technologies that may be used include electrodes, flow sensors, pressure sensors, photomultiplier tubes, CCDs, photodiode arrays, mass spectrometers, nuclear magnetic resonance, matrix assisted laser desorption ionization, UV-visible spectroscopy, Raman spectroscopy, fluorescence detection, chemiluminescence, and electrochemical detection.

Detection of physical parameters may be performed inferentially (e.g., pressure differential may be used to infer flow, etc.). Moreover, any of various conventional signal sampling, processing and/or transformation schemes including filtering (including low-pass, high-pass, or bandpass filtering), integration, and digital-to-analog conversion may be used. Detected physical parameters are used, whether directly or indirectly, to derive correction factors, as described in further detail below. Thus, resulting correction factors may be based the physical parameters either in substantially the form as measured or following any of various processing or conversion steps.

Introduction to Correction Method

To enhance the utility of parallel fluid processing systems, correction methods according to the present invention may be used to reduce variations in process conditions of parallel fluid processing systems among different process regions and/or among different experimental runs. For example, data obtained using process regions with slightly different performance characteristics may be corrected or normalized to mitigate such performance differences. Aside from overall performance or response, correction methods may be applied to discrete parameters such as, for example, fluid flow. In various embodiments, correction methods described herein permit any of: (1) more confident or meaningful comparison of process data obtained in a single experimental run from different fluid process regions; (2) more confident or meaningful comparison of process data obtained in different experimental runs from the same process region; and (3) easier identification of individual problematic process regions.

A flowchart outlining the steps 500 of a correction method according to one embodiment of the present invention is provided in FIG. 13. A first step 501 includes providing multiple flow-through fluid process regions, each containing solid material, in fluid communication with a common first fluid source through a splitting network and in fluid communication with at least one second fluid source. A second step 502 includes supplying a first fluid from the first fluid source to the fluid process regions at a selected first fluid source output flow rate. A third step 503 includes providing at least one detector in sensory communication with the multiple fluid process regions. A fourth step 504 includes supplying a calibrant to each fluid process region. A fifth step 505 includes processing the calibrant in each fluid process region according to a first fluid source output flow rate and a first fluid source composition profile. A sixth step 506 includes measuring a first physical parameter for each process region using the (at least one) detector. A seventh step 507 includes deriving at least one correction factor for each fluid process region based on the first physical parameter. An eighth step 508 includes supplying at least one second fluid to each fluid process region from the (at least one) second fluid source. A ninth step 509 includes processing the (at least one) second fluid in each fluid process region to obtain raw process data. A tenth step 510 includes applying the (at least one) correction factor for each fluid process region to the raw process data to yield corrected process data. Additional optional steps may further be employed. Any of the foregoing method steps may be automated. Steps that are particularly amenable to automation include the measuring, deriving, and applying steps, all of which may advantageously employ one or more microprocessors.

In a correction method according to the invention, each parallel fluid process region receives a calibrant. Substantially the same quantity and composition of calibrant is preferably provided to each fluid process region. Preferably, the calibrant is well-characterized to provide predictable and well defined process data upon being processed. In certain embodiments, the calibrant includes at least two components having different process characteristics relative to solid material(s) contained within the fluid process regions. For example, in a parallel analytical fluid processing system directed liquid chromatography, each process region may contain stationary phase separation media, and a calibrant may include a mixture of at least two components having different retention characteristics relative to the Separation media. In certain embodiments, the at least two components may both be retained components with different retention times, or one may be an unretained component with at least one other component being a retained component.

Correction Factor Derivation

Various correction schemes may be used with parallel fluid processing correction systems and methods according to the present invention. In one example, a preferred correction scheme utilizes least square fitting in the deriving step. Least square fitting is a mathematical procedure for finding the best fitting curve to a given set of points by minimizing the sum of the squares of the offsets ("the residuals") of the points from the curve. The method of least squares can be used to fit many different types of functions through a set of data points. Linear functions, exponential functions, power functions, or polynomial functions may be utilized in least square methods.

In one example, minimization or fitting based on vertical offsets from a line is preferred over fitting based on perpendicular offsets to simplify the analysis and permit easy generalization from a best-fit line to a best-fit polynomial. The linear least squares fitting technique is the simplest and most commonly applied form of linear regression and provides a solution to the problem of finding the best fitting straight line through a set of points.

Vertical least squares fitting proceeds by finding the sum of the squares of the vertical deviations $R^2$ of a set of n data points from a function f.

$$R^2 \Sigma [y_i - f(x_i, a_1, a_2, \ldots, a_n)]^2$$

The condition for $R^2$ to be a minimum is that (for $i=1, \ldots, n$)

$$\frac{\partial (R^2)}{\partial a_i} = 0$$

In the present example directed to a linear fit, $$f(a,b) = a + bx_i$$

so $$R^2(a, b) \equiv \sum_{i=1}^{n} [y_i - (a + bx_i)]^2$$

$$\frac{\partial (R^2)}{\partial a} = -2 \sum_{i=1}^{n} [y_i - (a + bx_i)] = 0$$

$$\frac{\partial (R^2)}{\partial b} = -2 \sum_{i=1}^{n} [y_i - (a + bx_i)] x_i = 0$$

These lead to the system of equations:

$$na + b \sum_{i=1}^{n} x_i = \sum_{i=1}^{n} y_i$$

$$a \sum_{i=1}^{n} x_i + b \sum_{i=1}^{n} x_i^2 = \sum_{i=1}^{n} x_i y_i$$

Solving the determinant of the matrix:

$$\begin{bmatrix} n & \sum_{i=1}^{n} x_i \\ \sum_{i=1}^{n} x_i & \sum_{i=1}^{n} x_i^2 \end{bmatrix} \begin{bmatrix} a \\ b \end{bmatrix} = \begin{bmatrix} \sum_{i=1}^{n} y_i \\ \sum_{i=1}^{n} x_i y_i \end{bmatrix}$$

then the coefficients are:

$$a = \frac{\sum_{i=1}^{n} y_i \sum_{i=1}^{n} x_i^2 - \sum_{i=1}^{n} x_i \sum_{i=1}^{n} x_i y_i}{n \sum_{i=1}^{n} x_i^2 - \left(\sum_{i=1}^{n} x_i\right)^2}$$

$$b = \frac{n \sum_{i=1}^{n} x_i y_i - \sum_{i=1}^{n} x_i \sum_{i=1}^{n} y_i}{n \sum_{i=1}^{n} x_i^2 - \left(\sum_{i=1}^{n} x_i\right)^2}$$

If vertical least square fitting is applied to a parallel fluid processing system with multiple fluid process regions in fluid communication with common fluid supply, preferably a set of discrete values for the correction factors (e.g., "a" and "b" above) is obtained for each process region. These correction factors may then be inserted into the appropriate equation (e.g., for a linear fit, "a+bx" as provided above) and used, for each fluid process region, to correct sets of raw fluid process data obtained from subsequent experimental runs to yield corrected fluid process data. If, for example, the raw fluid process data includes multiple data points that are plot on two axes to form a curve with multiple peaks, then a plot of the corrected fluid process data may typically include a curve of similar overall shape but may include different amplitudes and/or peak spacing.

While the foregoing example is directed to a linear fit, the derivation step of the present invention is not intended to be limited to using of any particular type of data fitting function. One skilled in the art will recognize that any of various data-fitting (e.g., curve-fitting) functions may be used. Integration functions may also be used to correct peak areas if desired. Additionally, while only two correction factors per process region were provided in the previous example, any appropriate or desirable number of correction factors may be used as dictated by the selected data-fitting function.

Multi-column Parallel Separation Devices

In one example of a parallel fluid processing system for providing analytical separation utility, a device includes multiple fluidically linked pressure-driven separation columns (i.e., linked to a common fluid supply via a splitting network) for performing liquid chromatography. As illustrated in FIGS. 4A–4B, one device 100 includes eight separation columns in fluid communication with a common mobile phase inlet by way of splitting network to permit multiple samples to be separated simultaneously using a minimum number of expensive system components, such as pumps, pulse dampers, etc. (Although FIGS. 4A–4B show the device 100 having eight separation columns 145A–145X, it will be readily apparent to one skilled in the art that any number of columns 145A–145X may be provided. For this reason, the designation "X" represents a variable and could represent any desired number of columns. This convention may be used hereinafter in this document.) Each separation column 145A–145X comprises a fluid processing region adapted to provide separation utility.

The device 100 may be constructed with nine substantially planar device layers 111–119, including multiple stencil layers 112–118. Each of the nine device layers 111–119 defines two alignment holes 120, 121, which are used in conjunction with external pins (not shown) to aid in aligning the layers 111–119 during construction, and/or to aid in aligning the device 100 with an external interface during a packing process.

The first device layer 111 defines several fluidic ports: two solvent inlet ports 122, 124 are used to admit (mobile phase) solvent to the device 100; eight sample ports 128A–128X permit sample to be introduced to eight columns (channels 145A–145X containing stationary phase material 147); a slurry inlet port 126 is used during a column packing process to admit slurry to the device 100; and a fluidic outlet port 130 that is used [1] during the packing process to exhaust (slurry) solvent from the device 100; and [2] during operation of the separation device 100 to carry effluent from the device 100. Alternatively, multiple outlet ports (not shown) may be provided to separately transport the effluent stream from each separation channel 145A–145X away from the device 100. Due to the sheer number of elements depicted in FIGS. 4A–4B, numbers for selected elements within alphanumeric series groups (e.g., individual sample inlet ports 128A–128X) are omitted from the drawings for clarity.

Each of the first through sixth layers 111–116 defines eight optical detection windows 132A–132X. Defining these windows 132A–132X through these device layers 111–116 facilitates optical detection by locally reducing the thickness of material bounding (from above and below) channel segments 170A–170X disposed downstream of the column-containing channels 145A–145X, thus reducing the amount of material between an external optical detector (not shown), such as a conventional UV-VIS detector, and the samples contained in the segments 170A–170X. Various types of optical detectors may be used to detect at least one property of a substance eluted from the packed separation channels 145A–145X.

The second through seventh layers 112–117 each define a first solvent via 122A for communicating a mobile phase solvent from a first mobile phase inlet port 122 to a first mobile phase channel 164 defined in the eighth layer 118, with further solvent vias 124A defined in the second through fifth layers 112–115 to transport a second mobile phase solvent to the channel 146 defined in the sixth layer 116. Additional vias 130A are defined in the second through sixth layers 112–116 to provide a fluid path between the fluidic port 130 and the effluent channel 162 defined in the seventh layer 117. A via 126A defined in the second layer 112 communicates slurry from the slurry inlet port 126 to a transverse channel 138 defined in the third layer 113 during a slurry packing process. Preferably, particulate material deposited by the slurry packing process fills not only the multiple separation channels 145A–145X, but also fills a manifold channel 142 and at least a portion of the channel 138. The second layer 112 further defines eight sample channels 135A–135X each having an enlarged region 134A–134X aligned with a sample inlet port 128A–128X defined in the first layer 111.

In addition to the structures described previously, the third layer 113 defines an elongate channel 138, and eight sample vias 136A–136X each aligned with the ends of a corresponding sample channel 135A–135X. The fourth layer 114 defines the manifold channel 142 and eight sample vias 144A–144X aligned with the vias 136A–136X in the third layer 113. The manifold channel 142 that provides fluid communication with the separation channels 145A–145X defined in the fifth layer 115 and the elongate channel 138 defined in the third layer 113. The separation channels 145A–145X preferably are about 40 mils (1 mm) wide or smaller. As an alternative to the manifold channel 142, a junction with radiating segments (not shown) could be used.

A porous (sample) frit 140 is disposed between the third layer 113 and fourth layer 114. The function of this frit 140 is to retain stationary phase material 147 in the separation channels 145A–145X, yet permit the passage of fluid when desired (i.e., fluidic samples supplied to the device 100 through the sample ports 128A–128X). Although various frit materials may be used, the frit 140 (along with frits 150, 151) is preferably constructed from a permeable polypropylene membrane, such as, for example, 1-mil thickness Celgard 2500 membrane (55% porosity, 0.209×0.054 micron pore size, Celgard Inc., Charlotte, N.C.), particularly if the layers 111–119 of the device 100 are bonded together using an adhesiveless thermal bonding method utilizing platens, such as described in commonly assigned U.S. Pat. No. 6,848,462, which is incorporated herein by reference. Preferably, the frit material has an average pore size that is smaller than the average particle size of the particulate to be packed within the device 100, so as to ensure that the packing material is retained within the device 100. Applicants have obtained favorable results using this specific frit material, without noticeable wicking or lateral flow within the frit despite using a single strip 140 of the frit membrane to serve multiple adjacent column-containing channels. As a less-preferred alternative to the single frit 140, multiple discrete frits (not shown) of various porous material types and thicknesses may be substituted.

The sixth layer 116 defines a channel 146 that communicates a second mobile phase solvent from vial 24A to the slit 152 defined in the seventh layer 117, which facilitates mixing of the two solvents in the channel 164 downstream of the slit 152. Further defined in the sixth layer 116 are eight vias 148A–148X for admitting mixed mobile phase solvent to the upstream ends of the separation channels 145A–145X, and a second set of eight vias 149A–149X at the downstream end of the same separation channels 145A–145X for transporting effluent from the downstream ends of the separation channels 145A–145X. Two frits 150, 151 are placed between the sixth and the seventh layers 116, 117. The first (mobile phase solvent) frit 150 is placed immediately above the first set of eight vias 148A–148X, while the second (mobile phase+sample) frit 151 is placed immediately above the second set of eight vias 149A–149X and below a similar set of eight vias 160A–160X defined in the seventh layer 117. The seventh layer 117 defines a channel segment 158, two medium forked channel segments 156A, 156B, and eight vias 154A–154X for communicating mobile phase solvent through the frit 150 and the vias 148A–148X to the separation channels 145A–145X defined in the fifth layer 115. The seventh layer 117 further defines a downstream manifold channel 162 that receives mobile phase solvent and sample during separation, and that receives (slurry) solvent during column packing, for routing such fluids through vias 130A to the fluidic exit port 130 defined in the first device layer 111.

The eighth layer 118 defines a mixing channel 164, one large forked channel segment 168, and four small forked channel segments 166A–166D. The eighth layer 118 further defines eight parallel channel segments 170A–170X downstream of the frit 151 for receiving effluent during separation or solvent during slurry packing, and for transporting such fluid(s) to the manifold channel 162 defined in the seventh layer 117. The ninth layer 119 serves as a cover for the channel structures defined in the eighth layer 118.

To prepare the device 100 for operation, the separation channels 145A–145X are packed with the desired stationary phase material. A preferred type of stationary phase material includes silica particles to which hydrophobic C-18 functional groups have been added. A slurry of a solvent (such as acetonitrile) and particulate is injected through the slurry inlet port 126 to ultimately pass into the channels 145A–145X. The frit 151 disposed at the end of the channels 145A–145X retains the particulate within the channels 145A–145X but permits the passage of solvent. Further details regarding particular column packing methods are provided in commonly assigned U.S. Pat. No. 6,923,907, which is hereby incorporated by reference.

To perform a chromatographic separation using the device 100, the packed device is placed in a chromatography instrument having a clamshell-type gasketed interface, such as described in commonly assigned U.S. Pat. No. 6,936,167. One, or more preferably two, solvents are initially provided to wet and/or equilibrate the device 100 through the first and second solvent inlet ports 122, 124. If two solvents are used (for example, to perform a gradient separation), then the solvents are layered one atop the other by way of the slit 152 within the mobile phase channel 164. (In an alternative embodiment, multiple mobile phase solvents may be supplied to an off-device micromixer (not shown) and supplied through a single solvent inlet port to the device.) The mobile phase is then split and distributed to each of the columns 145A–145X, and thereafter flows past the optical detection regions 132A–132X and out of the device 100 through the outlet port 130.

Once the device 100 is thoroughly wetted with mobile phase, the flow of mobile phase is suspended and samples are injected into the sample inlet ports 128A–128X. Once the samples are supplied to the device 100, the sample inlet ports 128A–128X are sealed and the flow of mobile phase is resumed, carrying the samples into the columns 145A–145X to perform the desired separation. Either isocratic separation (in which the mobile phase composition remains constant) or, more preferably, gradient separation (in which the mobile phase composition changes with time) may be performed. Analytical instruments, such as a conventional UV-Visible source and detector (not shown), may observe the results of the Separation through the optical detection regions 132A–132X. Alternatively, or additionally, the effluent may be collected from the device 100 for additional analysis. Although the device 100 depicts a single outlet port 130, multiple outlet ports (not shown; e.g., one port for each column 145A–145X) may be provided.

Figure 6C:
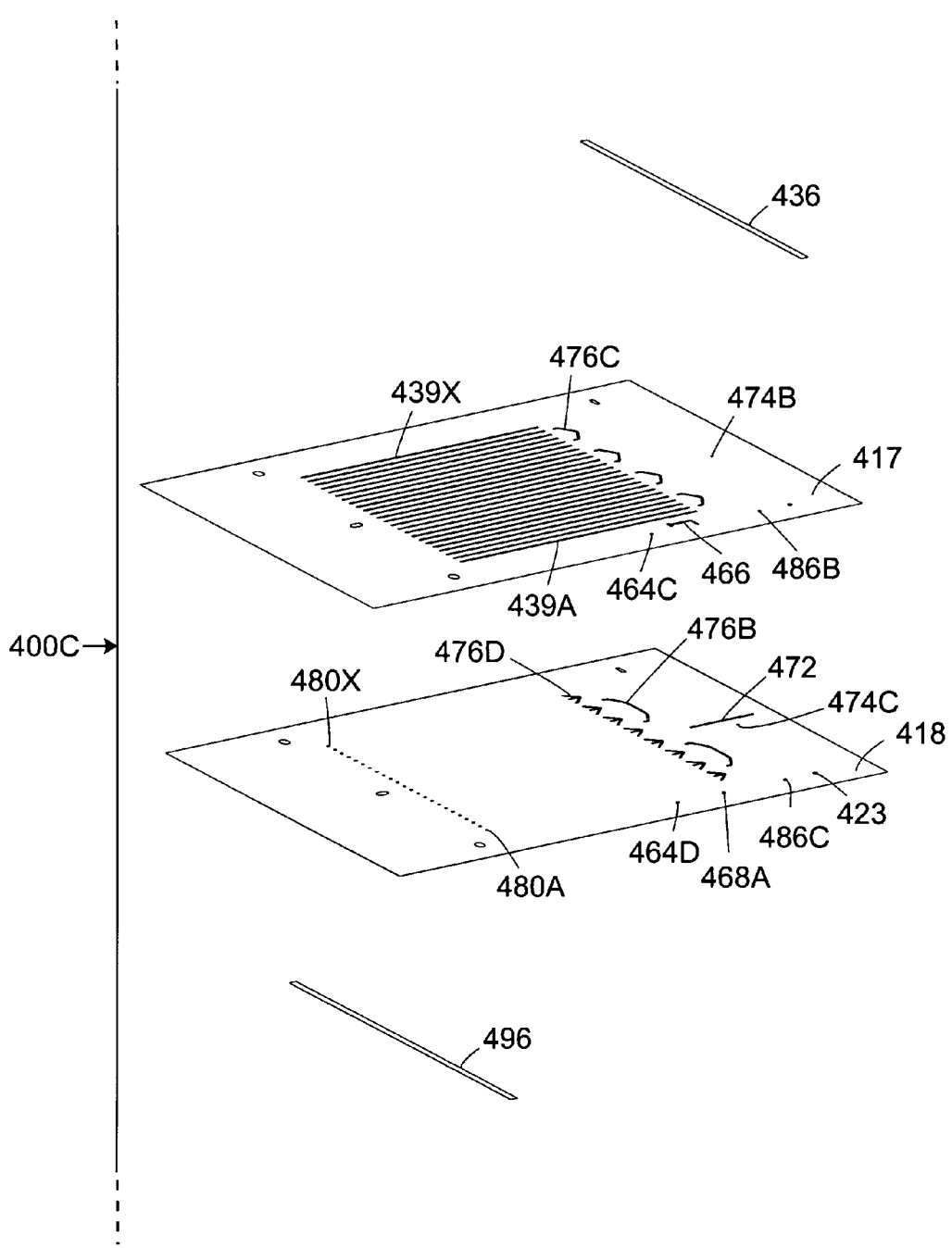
FIG. 6C is an exploded perspective view of a third portion, including the seventh and eighth layers, of the device shown in FIG. 5.
Figure 6D:
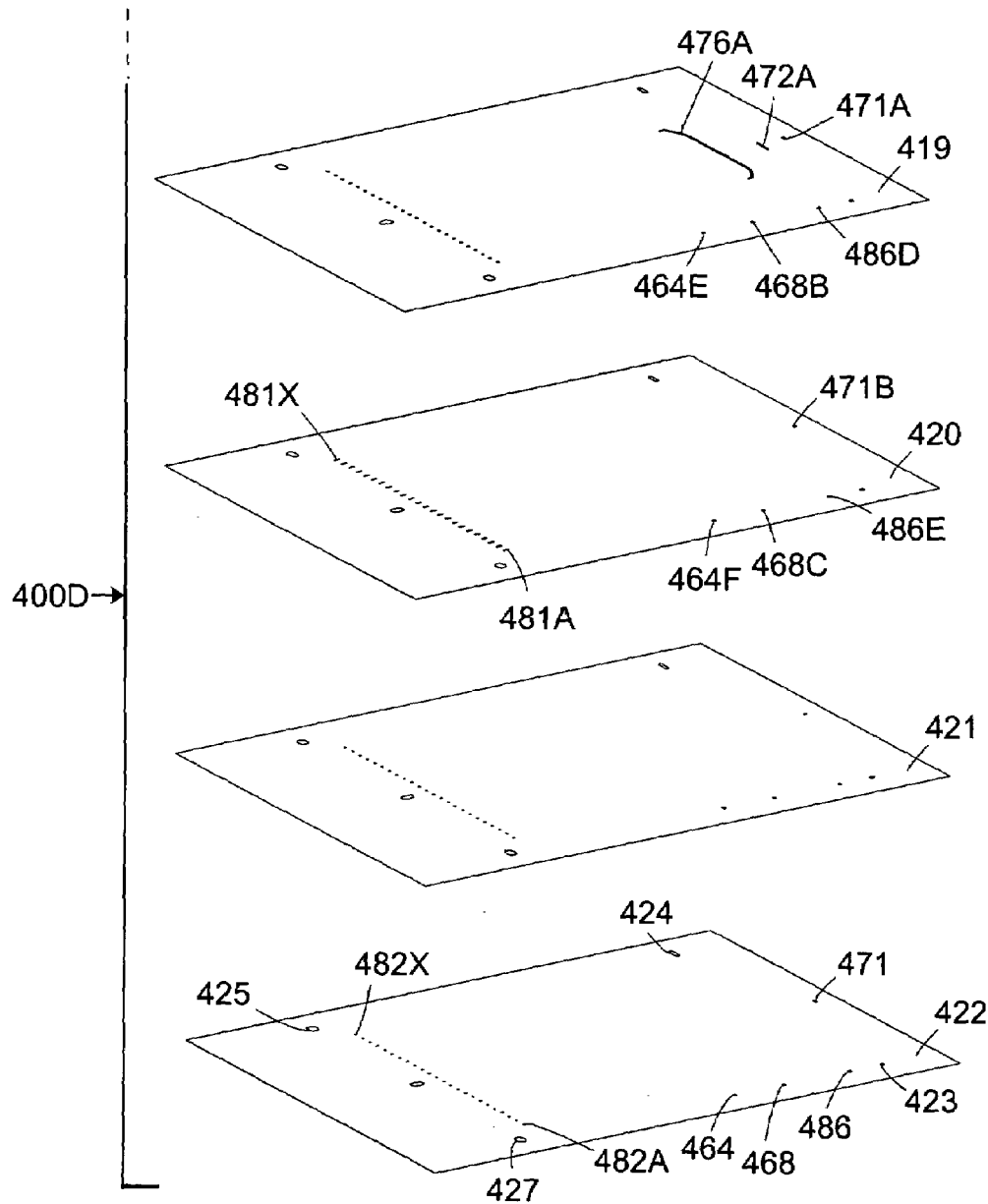
FIG. 6D is an exploded perspective view of a fourth portion, including the ninth through twelfth layers, of the device shown in FIG. 5.

In another example, a parallel fluid processing device adapted to provide (analytical) separation utility includes twenty-four separation columns and a different column outlet port for each separation column. One embodiment of such a device 400 is illustrated in FIG. 5 and FIGS. 6A–6E, with FIG. 6A illustrating a first portion 400A, FIG. 6B illustrating a second portion 400B, FIG. 6C illustrating a third portion 400C, and FIG. 6D illustrating a fourth portion 400D of the device 400. The device 400 includes twenty-four parallel separation channels 439A–439X containing stationary phase material (or columns 439A–439X) for performing liquid chromatography. The device 400 is constructed with twelve device layers 411–422, including multiple stencil layers 414–420 and two outer or cover layers 411, 422. Each of the twelve device layers 411–422 defines five alignment holes 423–427, which may be used in conjunction with external pins (not shown) to aid in aligning the layers during construction or in aligning the device 400 with an external interface (not shown) during a packing process or during operation of the device 400. Press-fit interconnects may be provided with either gasketed or gasketless interfaces. Preferably, the device 400 is constructed with materials selected for their compatibility with chemicals typically utilized in performing high performance liquid chromatography, including, water, methanol, ethanol, isopropanol, acetonitrile, ethyl acetate, dimethyl sulfoxide, and mixtures thereof. Specifically, the device materials should be substantially non-absorptive of, and substantially non-degrading when placed into contact with, such chemicals. Suitable device materials include polyolefins, such as polypropylene, polyethylene, and copolymers thereof, which have the further benefit of being substantially optically transmissive so as to aid in performing quality control routines (including checking for fabrication defects) and in ascertaining operational information about the device or its contents. For example, each device layer 411–422 may be fabricated from 7.5 mil (188 micron) thickness cast unoriented polypropylene (Copol International Ltd., Nova Scotia, Canada).

Broadly, the device 400 includes various structures adapted to distribute particulate-based slurry material among multiple separation channels 439A–439X (to become separation columns upon addition of stationary phase material), to retain the stationary phase material within the device 400, to mix and distribute mobile phase solvents among the separation channels 439A–439X, to receive samples, to convey eluate streams from the device 400, and to convey a waste stream from the device 400.

The first through third layers 411–413 of the device 400 are identical and define multiple sample ports/vias 428A–428X that permit samples to be supplied to channels 454A–454X defined in the fourth layer 414. While three separate identical layers 411–413 are shown (to promote strength and increase the aggregate volume of the sample ports/vias 428A–428X to aid in sample loading), a single equivalent layer (not shown) having the same aggregate thickness could be substituted. The fourth through sixth layers 414–416 define a mobile phase distribution network 450 (including elements 450A–450D) adapted to split a supply of mobile phase solvent among twenty-four channel loading segments 454A–454X disposed just upstream of a like number of separation channels (columns) 439A–439X. Upstream of the mobile phase distribution network 450, the fourth through seventh layers 414–417 further define mobile phase channels 448–449 and structures for mixing mobile phase solvents, including a long mixing channel 442, wide slits 460A–460B, alternating channel segments 446A–446V (defined in the fourth and sixth layers 414–416) and vias 447A–447W (defined in the fifth layer 415).

Preferably, the separation channels 439A–439X are adapted to contain stationary phase material, such as, for example, silica-based particulate material to which hydrophobic C-18 (or other carbon-based) functional groups have been added. One difficulty associated with conventional microfluidic devices has been retaining small particulate matter within separation columns during operation. The present device 400 overcomes this difficulty by the inclusion of a downstream porous frit 496 and a sample loading porous frit 456. Each of the frits 456, 496 (and frits 436, 438) may be fabricated from strips of porous material, e.g., 1-mil thickness Celgard 2500 polypropylene membrane (55% porosity, 0.209×0.054 micron pore size, Celgard Inc., Charlotte, N.C.) and inserted into the appropriate regions of the stacked device layers 411–422 before the layers 411–422 are laminated together. The average pore size of the frit material should be smaller than the average size of the stationary phase particles. Preferably, an adhesiveless bonding method, such as one of the methods described previously herein, is used to interpenetrably bond the device layers 411–422 (and frits 436, 438, 456, 496) together. Such methods are desirably used to promote high bond strength (e.g., to withstand operation at high internal pressures of preferably at least about 100 psi (690 kPa), more preferably at least about 500 psi (3450 kPa)) and to prevent undesirable interaction between any bonding agent and solvents and/or samples to be supplied to the device 400.

A convenient method for packing stationary phase material within the separation channels 439A–439X is to provide it in the form of a slurry (i.e., particulate material mixed with a solvent, such as acetonitrile). Slurry is supplied to the device 400 by way of a slurry inlet port 471, corresponding vias 471A, 471B, and channel structures defined in the seventh through ninth device layers 417–419. Specifically, the ninth layer 419 defines a slurry via 471A, a waste channel segment 472A, and a large forked channel 476A. The eighth device layer 418 defines two medium forked channels 476B and a slurry channel 472 in fluid communication with the large forked channel 476A defined in the ninth layer 419. The eighth layer 418 further defines eight smaller forked channels 476D each having three outlets, and twenty-four column outlet vias 480A–480X (further defined in the ninth layer 419) leading to segments 481A–481X defined in the tenth layer 420 and therafter to outlet ports 482A–482X defined in the twelfth layer 422. The seventh layer 417 defines four small forked channels 476C in addition to the separation channels 439A–439X. In the aggregate, the large, medium, small, and smaller forked channels 476A–476D form a slurry distribution network that communicates slurry from a single inlet (e.g., slurry inlet port 471) to twenty-four separation channels 439A–439X (to become separation columns 439A–439X upon addition of stationary phase material). Upon addition of particulate-containing slurry to the separation channels 439A–439X, the particulate stationary phase material is retained within the separation channels by one downstream porous frit 496 and by one sample loading porous frit 456. After stationary phase material is packed into the columns 439A–439X, a sealant (preferably substantially inert such as UV-curable epoxy) may be added to the slurry inlet port 471 to prevent the columns from unpacking during operation of the device 400. The addition of sealant should be controlled to prevent blockage of the waste channel segment 472A.

As an alternative to using packed particulate material, porous monoliths may be used as the stationary phase material. Generally, porous monoliths may be fabricated by flowing a monomer solution into a channel or conduit, and then activating the monomer solution to initiate polymerization. Various formulations and various activation means may be used. The ratio of monomer to solvent in each formulation may be altered to control the degree of porosity Of the resulting monolith. A photoinitiator may be added to a monomer solution to permit activation by means of a lamp or other radiation source. If a lamp or other radiation source is used as the initiator, then photomasks may be employed to localize the formation of monoliths to specific areas within a fluidic separation device, particularly if one or more regions of the device body are substantially optically transmissive. Alternatively, chemical initiation or other initiation means may be used. Numerous recipes for preparing monolithic columns suitable for performing chromatographic techniques are known in the art. In one embodiment, a monolithic ion-exchange column may be fabricated with a monomer solution of about 2.5 ml of 50 millimolar neutral pH sodium phosphate, 0.18 grams of ammonium sulfate, 44 microliters of diallyl dimethlyammonium chloride, 0.26 grams of methacrylamide, and 0.35 grams of piperazine diacrylamide.

To prepare the device 400 for operation, one or more mobile phase solvents may be supplied to the device 400 through mobile phase inlet ports 464, 468 defined in the twelfth layer 422. These solvents may be optionally pre-mixed upstream of the device 400 using a conventional micromixer and then supplied to the device though only a single inlet port. Alternatively, these solvents may be conveyed through several vias (464A–464F, 468A–468C) before mixing. One solvent is provided to the end of the long mixing channel 442, while the other solvent is provided to a short mixing segment 466 that overlaps the mixing channel 442 through wide slit 460A defined in the sixth layer 416 and wide slit 460B defined in the fifth layer 415. One solvent is layered atop the other across the entire width of the long mixing channel 442 to promote diffusive mixing. To ensure that the solvent mixing is complete, however, the combined solvents also flow through an additional mixer composed of alternating channel segments 446A–446V and vias 447A–447W. The net effect of these alternating segments 446A–446V and vias 447A–447W is to cause the combined solvent stream to contract and expand repeatedly, augmenting mixing between the two solvents. The mixed solvents are supplied through channel segments 448, 449 to the distribution network 450 inclusive of one large forked channel 450A each having two outlets, two medium forked channels 450B each having two outlets, four small forked channels 450C each having two outlets, and eight smaller forked channels 450D each having three outlets.

Each of the eight smaller forked channels 450D is in fluid communication with three of twenty-four sample loading channels 454A–454X. Additionally, each sample loading channel 454A–454X is in fluid communication with a different sample loading port 428A–428X. Two porous frits 438, 456 are disposed at either end of the sample loading channels 454A–454X. While the first frit 438 technically does not retain any packing material within the device, it may be fabricated from the same material as the second frit 456, which does retain packing material within the columns 439A–439X by way of several vias 455A–455X, 457A–457X. To prepare the device 400 for sample loading, solvent flow is temporarily interrupted, an external interface (not shown) previously covering the sample loading ports 428A–428X is opened, and samples are supplied through the sample ports 428A–428X into the sample loading channels 454A–454X. The first and second frits 438, 456 provide a substantial fluidic impedance that prevents fluid flow through the frits 438, 456 at low pressures. This ensures that the samples remain isolated within the sample loading channels 454A–454X during the sample loading procedure. Following sample loading, the sample loading ports 428A–428X are again sealed (e.g., with an external interface) and solvent flow is re-initiated to carry the samples onto the separation columns 439A–439X defined in the seventh layer 417.

While the bulk of the sample and solvent that is supplied to each column 439A–439X travels downstream through the columns 439A–439X, a small split portion of each travels upstream through the columns in the direction of the waste port 485. The split portions of sample and solvent from each column that travel upstream are consolidated into a single waste stream that flows through the slurry distribution network 476, through a portion of the slurry channel 472, then through the short waste segment 472A, vias 474C, 474B, a frit 436, a via 484A, a waste channel 485, vias 486A–486E, and through the waste port 485 to exit the device 400. The purpose of providing both an upstream and downstream path for each sample is to prevent undesirable cross-contamination from one separation run to the next, since this arrangement prevents a portion of a sample from residing in the sample loading channel during a first run and then commingling with another sample during a subsequent run.

Either isocratic separation (in which the mobile phase composition remains constant) or, more preferably, gradient separation (in which the mobile phase composition changes with time) may be performed. If multiple separation columns are provided in a single integrated device (such as the device 400) and the makeup of the mobile phase is subject to change over time, then at a common linear distance from the mobile phase inlet it is desirable for mobile phase to have a substantially identical composition from one column to the next. This is achieved with the device 400 due to two factors: (1) volume of the path of each (split) mobile phase solvent substream is substantially the same to each column; and (2) each flow path downstream of the fluidic (mobile phase and sample) inlets is characterized by substantially the same impedance. The first factor, substantially equal substream flow paths, is promoted by design of the mobile phase distribution network 459. The second factor, substantial equality of the impedance of each column, is promoted by both design of the fluidic device 400 (including the slurry distribution network 476) and the fabrication of multiple columns 439A–439X in fluid communication (e.g., having a common outlet) using the slurry packing method disclosed herein. Where multiple columns are in fluid communication with a common outlet, slurry flow within the device is biased toward any low impedance region. The more slurry that flows to a particular region during the packing process, the more particulate is deposited to locally elevate the impedance, thus yielding a self-correcting method for producing substantially equal impedance from one column to the next.

While the embodiment illustrated in FIG. 5 and FIGS. 6A–6E represents a preferred fluidic device, one skilled in the art will recognize that devices according to a wide variety of other designs may be used, whether to perform parallel liquid chromatography or other fluid phase separation processes. For example, other functional structures, such as, but not limited to, sample preparation regions, fraction collectors, splitters, reaction chambers, catalysts, valves, mixers, and/or reservoirs may be provided to permit complex fluid handling and analytical procedures to be executed within a single device and/or system.

Typical (Uncorrected) Results from Operating First Parallel Separation Device

As mentioned previously, a typical output of a chromatographic separation is a plot called a chromatogram. If UV-VIS detection is used, then the may include a plot of absorbance units versus time. Other types of detection technologies and unit scales may be used. One example of a simple chromatogram obtained from separating Applicants' standard test mixture in one separation column is provided in FIG. 7. Notably, FIG. 7 contains five peaks (local maxima), each corresponding to a region of elevated concentration of a species (e.g., uracil or parabens). When the same sample mixture is separated in multiple fluidically linked columns, however, and the resulting chromatograms are superimposed, significant variation between individual chromatograms typically appears. FIG. 8 shows a composite chromatogram obtained from eluting Applicants' standard test mixture in a fluidically linked parallel multi-column device substantially similar to the device 400 of FIG. 5 and FIGS. 6A–6E. For the sake of clarity, results from only three of the twenty-four separation columns are provided in FIG. 8. Significant column-to-column variation is apparent in FIG. 8; it would be desirable to significantly reduce this variation for the reasons enumerated above. Correction methods described herein may be used to correct various data resulting from the operation of parallel process regions. For example, in the context of parallel separation, correction may be applied to retention times, peak areas, and other desirable measures.

Method for Correcting Retention Times in Parallel Chromatography

A flowchart outlining the steps 550 of a method for correcting retention times in a parallel liquid chromatography according to the present invention is provided in FIG. 14. A first step 551 includes providing multiple liquid chromatography columns each containing stationary phase material and having an associated detection region. A second step 552 includes supplying, to each column, a first calibration mixture containing at least a first component and a second component having different retention characteristics relative to the stationary phase material. A third step 553 includes eluting, in each column, the at least first component and second component according to a first mobile phase source output flow rate and a first mobile phase composition profile. A fourth step 554 includes measuring, for each column, a first time for the first component to reach the associated detection region and a second time for the retained component to reach the associated detection region. This measurement may be performed optically (e.g. via UV-visible detection) if desired. As noted previously, the time corresponding to a local maximum or peak on the chromatogram is called the retention time for that component. A fifth step 555 includes deriving, for each column, at least one correction factor based on the first time and the second time. A sixth step 556 includes supplying, for each column, at least one sample mixture containing multiple sample components. A seventh step 557 includes eluting, in each column, at least two components of the sample mixture to obtain raw chromatographic data. An eighth step 558 includes applying, for each column, the at least one correction factor to the raw chromatographic data to yield corrected chromatographic data with corrected retention times. In a preferred method, the correction includes normalizing the retention times obtained from each column (process region) to a curve obtained by methods described herein or equivalent methods known in the art.

A wide variety of samples may be used with methods and systems according to the present invention. Typically, a known, well-characterized calibrant is provided to each of the fluidically linked columns to perform the first elution, and the second elution step involves providing a different sample to each column. The calibrant preferably has at least two components having different retention characteristics relative to the stationary phase material. Combinations of components having different retention characteristics include two retained components having different retention times, or one retained component and one unretained component. Samples with substantially the same composition may be provided to multiple columns simultaneously to provide multiple data sets for the same mixture. Additionally, the calibrant and sample may also be of substantially the same composition, although the utility of such operation is limited.

Preferably, any of the method steps may be automated. Steps that are particularly amenable to automation include the measuring, deriving, and applying steps, since they advantageously employ a microprocessor, such as contained within a personal computer or other conventional processing device.

An optional further step includes cleaning the columns between the first elution step and the second elution step. Particularly when gradient separation is used (e.g., for reverse phase separation), the cleaning step may include maintaining a mobile phase composition profile with a high concentration of organic solvent to release any highly retained species. To provide cleaning utility, a desirable mobile phase composition would be at least fifty percent organic; more preferably at least seventy percent organic; more preferably still at least eighty percent organic; and further preferably at least ninety percent organic. The cleaning step may be performed following the first elution as a distinct step, or it may occur by simply maintaining a high organic concentration attained at the end of gradient separation for a prolonged period.

As noted previously, either isocratic or gradient separation may be performed with systems and methods according to the present invention. Desirable gradients may include varying the weight percent of at least one solvent (e.g., an organic solvent, such as acetonitrile), or varying the concentration of a solute in the mobile phase. If the composition of the mobile phase is to be varied to perform gradient elution, then the common mobile phase source preferably includes discrete fluidic reservoirs and multiple pumps capable of being controlled independently.

The multiple columns may be interconnected conventional tubular columns such as illustrated in FIG. 3, or, more preferably, may be multiple (preferably microfluidic) columns integrated within a single device such as the devices 100, 400 illustrated in FIGS. 4A–4B and FIG. 5 and FIGS. 6A–6E. The detection regions may be disposed within the same device as the columns (e.g., the detection regions 132A–132N in the device 100) or may be disposed separately, such as within a flow cell (not shown) used in conjunction with the device 400 illustrated in FIG. 5 and FIGS. 6A–6E. One example of a desirable detection format includes the multi-channel flow cells described in commonly assigned U.S. Pat. No. 6,867,857, which is incorporated herein by reference.

Deriving Correction Factors for Retention Time Correction

As noted previously, vertical least square fitting is but one preferred method for deriving correction factors to be used in parallel fluid processing correction systems and methods.

The coefficients derived previously for a linear vertical least square fit are:

$$a = \frac{\sum_{i=1}^{n} y_i \sum_{i=1}^{n} x_i^2 - \sum_{i=1}^{n} x_i \sum_{i=1}^{n} x_i y_i}{n \sum_{i=1}^{n} x_i^2 - \left(\sum_{i=1}^{n} x_i\right)^2}$$

$$b = \frac{n \sum_{i=1}^{n} x_i y_i - \sum_{i=1}^{n} x_i \sum_{i=1}^{n} y_i}{n \sum_{i=1}^{n} x_i^2 - \left(\sum_{i=1}^{n} x_i\right)^2}$$

To apply these equations to data obtained from a parallel chromatography method to correct retention times, the variables are defined as follows:

n=the number of peaks (eluted components) present in the mixture x=raw retention time (column-specific, for each eluted component)

y=average retention time (for each eluted component)

Discrete values for the correction factors "a" and "b" are obtained for each column of a fluidically linked parallel chromatography system. For example, assume that a calibration mixture, such as Applicant's standard test mixture comprising uracil and four parabens (totaling five components), is supplied to each column of a fluidically linked twenty-four column liquid chromatography system having a common mobile phase supply, such as the device 400 of FIG. 5 and FIGS. 6A–6E. In this case, "n" would be equal to five. Raw retention times are column-specific. Each column would produce five raw retention times, with each retention time corresponding to one sample component. For example, in the first separation column, the raw retention times for sample components one through five may be designated by $x_1$, $x_2$, $x_3$, $x_4$, and $x_5$, respectively. Repeating the process for all 24 columns provides 24 sets of five retention times ($x_1$, $x_2$, $x_3$, $x_4$, $x_5$). All twenty-four $x_1$ values are averaged to yield $y_1$ (the average retention time for component 1), all twenty-four $x_2$ values are averaged to yield $y_2$ (the average retention time for component 2), and so on, to obtain an average retention time for each eluted component (i.e., $y_1$, $y_2$, $y_3$, $y_4$, $y_5$) in the system. Applying the preceding values to the last two equations provided above, values for "a" and "b" can be derived for each column to yield twenty-four sets of correction factors (i.e., [$a_1$, $b_1$], [$a_2$, $b_2$], [$a_3$, $b_3$], . . . [$a_{24}$, $b_{24}$]). These correction factors may then be inserted in the linear equation above (i.e., "a+bx") used to correct the first set of raw chromatographic data (namely, the time for each raw data point including the raw 'peak' retention times) and subsequent sets of data obtained from the same columns of the fluidically linked multi-column system, no matter what type of samples are provided to the columns following the calibration run. That is, each raw data point in the chromatogram includes an absorbance value (amplitude) versus time. The chromatogram includes many data points (depending on the sampling rate), including a 'peak' (local maximum) absorbance values for each sample component. All of the raw data may be corrected to yield corrected chromatograms having corrected retention times. Notably, in this specific example, the absorbance values do not change following correction; rather, only the time portion of each data point is subject to change.

EXAMPLE

Parallel Chromatography Retention Time Correction Method

An example applying the foregoing least square fitting method is provided in FIGS. 12A–12E. FIG. 12A is a table providing raw retention times for a first separation of Applicants' standard test mixture in a twenty-four column microfluidic device substantially similar to the design of the device 400 illustrated and described in connection with FIG. 5 and FIGS. 6A–6E. Retention times ("x-values") for each of the five components of Applicants' standard test mixture are provided for each of the twenty-four columns, with average values ("y-values") for each retention time provided below the raw data. Absorbance values corresponding to the retention times were recorded, but have been omitted for the sake of clarity from FIG. 12A. The superimposed raw chromatogram corresponding to the raw retention times provided in FIG. 12A is depicted at FIG. 10. Notably, significant column-to-column variability is apparent.

FIG. 12B is a table of two correction factors for each column of the twenty-four fluidically linked columns, the factors being derived from the raw retention times using the least square fit method described above. Each raw retention time value in FIG. 12A was corrected by inserting the corresponding correction factors (from FIG. 12B) into the equation "a+bx". FIG. 12C is a table providing the resulting corrected retention times. The superimposed corrected chromatogram having corrected retention times (corresponding to the corrected retention times provided in FIG. 12C) is depicted at FIG. 11. As compared to FIG. 10, a dramatic reduction in variability is immediately apparent.

After the correction factors have been derived from the foregoing calibration run, they may be applied to subsequent runs performed on the same set of fluidically linked columns, no matter what type of sample is used. In real-world applications, samples will usually be substantially different from the calibrant. For the sake of illustration, however, Applicants performed a second run using the same mixture as used in the first fun (i.e., Applicants' standard test mixture). The raw chromatographic data resulting from the second run is provided in FIG. 12D. Thereafter, the correction factors from FIG. 12B were applied to the raw data of FIG. 12D to yield corrected chromatographic data having corrected retention times, the corrected data being provided in FIG. 12E.

EXAMPLE

Parallel Chromatography Peak Area Correction

In another example directed to parallel separation using multiple analytical process regions (e.g., columns) fluidically connected to a common fluid supply, peak areas may be corrected. Peak area correction permits improved quantitative comparison between columns—such as to account for variations in any of sample injection volume, column packing density, and column flow in a parallel column system with a common fluid supply.

A multi-column device or system as described previously (e.g., such as the device 400 of FIG. 5 and FIGS. 6A–6E) may be operated to obtain time-dependent data such as (for example) absorbance versus time. Individual peaks (local maxima) may be determined with derivatives and inflection points. For purposes of locating each peak among multiple peaks obtained from a given run in a given column, a preferred method includes the determination of five points—two minima, one maximum, and two inflection points. Baseline correction is then performed (e.g., using numerical methods) to eliminate drift. Following baseline correction, peak areas may be computed numerically by integration.

In one method for peak area correction, a common calibrant is supplied to each column of a fluidically linked parallel multi-column device or system. Preferably, the calibrant includes at least two components with different retention characteristics. In one embodiment, a calibrant may include three peaks. For each column in the calibration run, the peak areas are determined. Then the areas of the three peaks of each column are averaged together to obtain an average peak area for each column. The individual column average peak areas are then averaged together to yield an overall run average for all of the columns. The corresponding correction factors are calculated for each column by dividing the overall run average by the corresponding column average to yield one correction factor per column. Then, for each subsequent run, the raw peak area for each column is multiplied by its corresponding correction factor to obtain a corrected peak area.

One example of a peak area correction method applied to a twenty-four column parallel separation device (substantially similar to the device 400 described in connection with FIG. 5 and FIGS. 6A–6E) may be described in connection with FIGS. 15A–15B and FIGS. 16A–16B. FIG. 15A is a table including raw peak areas and correction factors obtained from a first (calibration) run by separating Applicant's standard test mixture in each column of a twenty-four column parallel separation device. Individual peak areas for peaks 2–5 obtained from each column were computed numerically as described previously. Data for the unretained uracil peak was omitted. After the individual peak areas for peaks 2–5 were determined, these areas were averaged for each column. Thereafter, these column-specific average areas were averaged to yield an overall run average peak area of 105.9 (inclusive of peaks 2–5 obtained from all columns). The corresponding correction factors are calculated for each column by dividing the overall run average area (105.9) by the corresponding column average to yield one correction factor per column, with the resulting correction factors ranging in value from about 0.844 to about 1.199. Following the calibration run and correction factor derivation, a second run was performed. While Applicant's standard test mixture was used for the second run, in a real-world application it would be more desirable and useful to separate a different sample or group of samples in the second run. Raw peak areas were determined for the second run. For the sake of simplicity, only data from the third (ethyl paraben) peak is presented in FIG. 15B. On a column-specific basis, the raw peak area is then multiplied by the appropriate correction factor to obtain a corrected peak area. The effect of such correction may be seen in FIGS. 16A–16B. FIG. 16A depicts raw peak 3 area (for both runs 1 and 2) as a function of column number, while FIG. 16B depicts corresponding corrected values. Notably, the peak area variability is significantly reduced. Column-to-column peak area % CV improved by a factor of 2.4 when peak area corrections were applied.

EXAMPLE

Parallel Chromatography Retention Time Correction System

While various combinations of elements may be employed in a system for correcting data (e.g., retention times, peak areas, or other desirable values) in multi-column liquid chromatography, one example is provided in FIG. 17. The system 600 includes two solvent reservoirs 601, 602 in fluid communication with a degasser 604 and at least one (more preferably at least two) pump(s) 605. A pulse damper 608 is preferably provided downstream of true pump(s) 605 to reduce variations in the mobile phase supply pressure. A mixer (not shown) is preferably disposed between the pump(s) and the fluidically linked separation columns. A multi-column separation device 610 (such as the integrated microfluidic devices 100, 400 or fluidically linked conventional columns 10A–10N) may be used. Calibrant or mobile phase may be provided to the separation device 610 through a calibrant/sample supply 618, which may include multiple conventional loop-type injection valves for providing pressurized pre-column injection, or a multi-well micropipettor for providing on-column injection to a planar microfluidic device (e.g., the devices 100, 400). As described previously, calibrant is preferably provided in a first run to permit correction factors to be derived, and then sample is provided to the columns in subsequent runs to which the correction factors are applied.

Multiple detection regions 615, each being associated with one separation column, are preferably disposed downstream of the separation columns, and such regions 615 may be either integrated into the device 610 or provided in a separate element, such as a multi-channel flow cell. Preferably, each detection region 615 includes a substantially optically transmissive region for permitting the transmission of electromagnetic radiation (e.g., ultraviolet light) of a desired wavelength. At least one detector 620 is provided in sensory communication with the detection regions 615; the detector 620 preferably includes an electromagnetic source and an electromagnetic receiver. Fiber optic conduits may be advantageously employed to direct electromagnetic radiation of a desired wavelength to and/or from the detection region 615, as described in commonly assigned U.S. Pat. No. 6,867,857.

A microprocessor 625 and compatible data storage element 626 are provided, with at least one of the two receiving chromatographic output information (e.g., absorbance versus time) from the detector 620. Various conventional microprocessors, including those present in personal computing devices, may be employed. The data storage element 626 may advantageously include a hard disk drive, random access memory, or other conventional data storage media known in the computing arts. The data storage element 626 could also be integrated with the microprocessor 625, such as in the form of an internal memory cache. The microprocessor 625 executes a set of operating instructions to derive correction factors based on data obtained from the detector 620, and to apply the correction factors to generate corrected chromatographic data. One or more display 628 and input devices 629 are preferably provided to permit the user to monitor the chromatographic process and interact with the microprocessor 625.

Parallel Synthesis

The preceding microfluidic devices 100, 400 may be adapted for use in parallel synthesis by substituting catalyst material for stationary phase material to form reactor beds instead of separation columns. One or more reagents may be added to the devices 100, 400 to provide parallel synthesis utility, and the foregoing data correction methods may be applied to data gathered during their operation. Notably, the devices 100, 400 include fluid process regions in fluid communication with a common slurry inlet for supplying the same particulate material to each channel to promote similar performance by each parallel fluid process region.

In another embodiment, parallel fluid process regions may be provided with different performance characteristics, such as by providing different solid materials to different fluid process regions in a single device or system. FIGS. 18A–18G illustrate a parallel fluid processing device 810 having two groups of three process regions, with each group of process regions having a separate solid distribution network to promote different process conditions in each group of process regions. This may be useful, for example, in methods development.

Figure 18D:
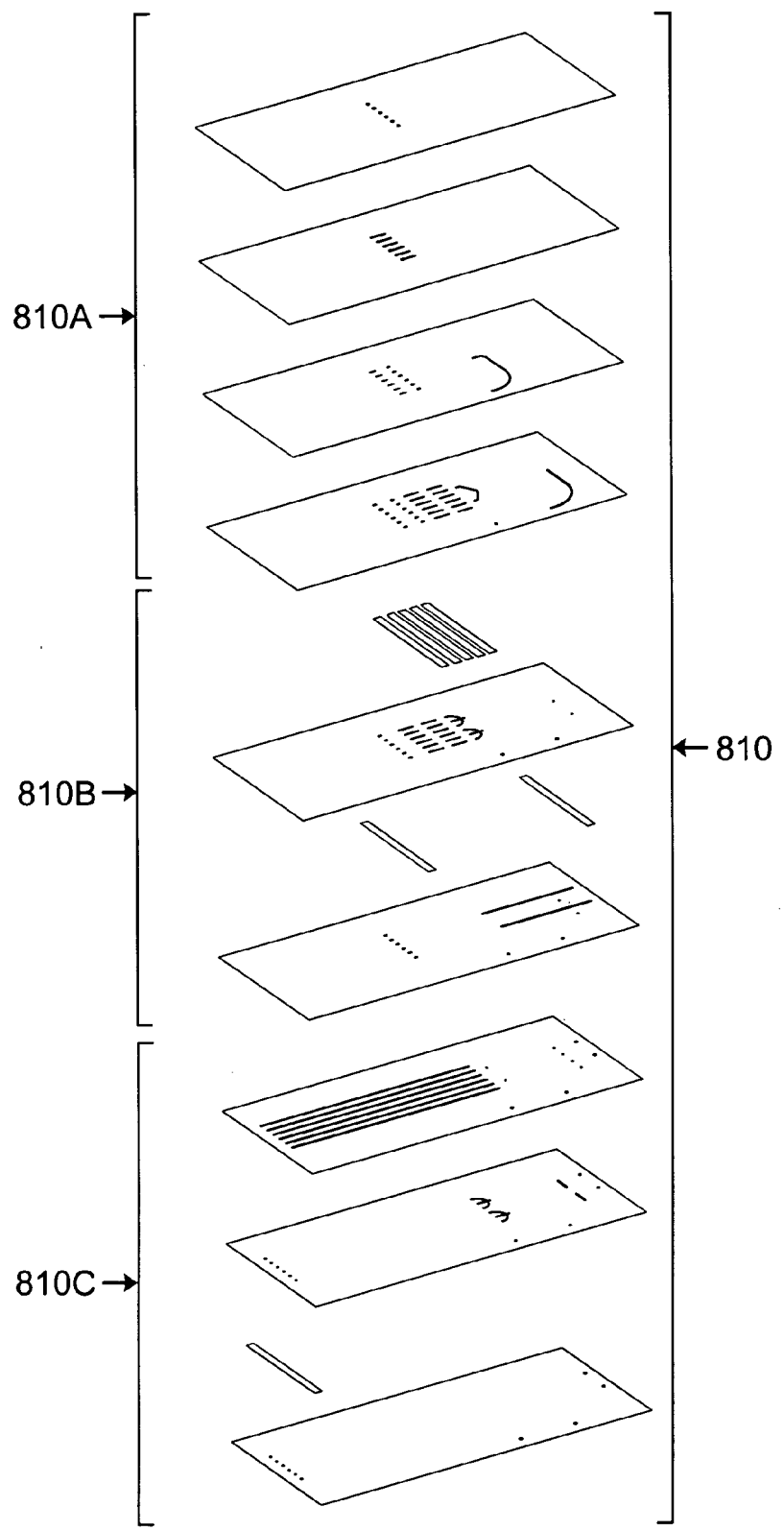
FIG. 18D is a reduced scale composite of FIGS. 18A–18C showing an exploded perspective view of the device of FIGS. 18A–18C.

FIG. 18A illustrates a first portion 810A of the device 810, FIG. 18B illustrates a second portion 810B of the device 810, FIG. 18C illustrating a third portion 810C of the device 810, and FIG. 18D illustrates the three portions 810A–810C in composite. The device 810 includes six parallel process channels 828A–828N containing solid material. In one embodiment, the solid material comprises catalyst material. The device 810 is constructed with nine device layers 811–819, including multiple stencil layers 812–818 and two outer or cover layers 811, 819. Press-fit interconnects may be provided with either gasketed or gasketless interfaces. Preferably, the device 810 is constructed with materials selected for their compatibility with chemicals to be used in the desired fluid process.

Broadly, the device 810 includes various structures adapted to distribute particulate-based slurry material among multiple fluid process channels 828A–828N, to retain the solid material within the device 810, to distribute common reagents or solvents among the fluid process channels 828A–828N, to receive (different) reagents or samples, to convey effluent reaction products or eluate from the device 810, and to convey a waste stream from the device 810.

Preferably, the fluid process channels 828A–828N are adapted to contain solid material, such as catalyst material or stationary phase material, either of which may be preferably particulate-based. To retain this solid material within the fluid process channels 828A–828N, the device 810 includes a downstream porous element 831, a sample/reagent loading porous element 859, and a waste solvent porous element 884. Each porous element 831, 859, and 884 (and porous elements 877A–877N) may be fabricated from a strip of porous material, e.g., 1-mil thickness Celgard 2500 polypropylene membrane (55% porosity, 0.209×0.054 micron pore size, Celgard Inc., Charlotte, N.C.) and inserted into the appropriate regions of the stacked device layers 811–819 before the layers 811–819 are joined together. The average pore size of the porous material should be smaller than the average size of the solid particles. Preferably, an adhesiveless bonding method, such as one of the methods described previously herein, is used to interpenetrably bond the device layers 811–819 (and porous elements 831, 859, 884, and 877A–877N) together to promote high bond strength and compatibility with a range of different reagents and/or solvents.

A convenient method for packing solid material within the fluid process channels 828A–828N is to provide it in the form of a slurry (e.g., particulate material mixed with a solvent). Slurry is supplied to the device 810 by way of slurry inlet ports 820A, 820B and channel structures defined in the sixth through eighth device layers 816–818. Specifically, the eighth layer 818 defines slurry vias 821A, 821B, solvent waste channel segments 836A, 836B, two small forked channels 826A and 826B and six fluid process channel outlet vias 830A–830N. The seventh device layer 817 defines slurry vias 822A, 822B, and the fluid process channels 828A–828N. The sixth device layer 816 defines slurry channels 823A, 823B in fluid communication with the small forked channels 826A and 826B (by way of two vias 825A, 825B in the seventh layer 817) and the slurry vias 822A, 822B defined in the seventh layer 817. In the aggregate, the slurry channel 823A and small forked channel 826A form a first slurry distribution network that communicates slurry from the slurry inlet 820A to a first group of three fluid process channels 828A–828C. In addition, a separate second slurry distribution network is formed by slurry channel 823B and small forked channel 826B that communicates slurry from the slurry inlet 820B to a second group of three fluid process channels 828D–828N. Each slurry distribution network may be filled with a different (or similar, if desired) type of packing material. The slurry may be added by stirring the solid material in a carrier solvent so that a suspension is formed, and then pumping this continually stirred suspension into the slurry inlet port at a fixed pressure. Upon addition of particulate-containing slurry to the fluid process channels 828A–828N, the solid material is retained within the fluid process channels by one downstream porous element 831, one sample/reagent loading porous element 859, and one solvent waste porous element 884. After solid material is packed into the fluid process channels 828A–828N, a sealant (preferably substantially inert, such as UV-curable epoxy) may be added to the slurry inlet ports 820A, 820B to prevent the fluid process channels 828A–828N from unpacking during operation of the device 810. The addition of sealant should be controlled to prevent blockage of the solvent waste channel segments 836A, 836B.

The first layer 811 of the device 810 defines multiple sample/reagent ports 852A–852N that permit different samples/reagents to be supplied to each of the multiple sample/reagent loading channels 850A–850N defined in the second layer 812. The third through sixth layers 813–816 define a common reagent/mobile phase solvent distribution network designed to push the different samples/reagents onto each of the six separation channels 828A–828N. Each sample/reagent loading channel 850A–850N is in fluid communication with a different sample/reagent loading port 852A–852N. The commonly supplied liquid (common reagent or mobile phase solvent, either of which may include a mixture of two or more liquids) flows from the inlet port 890 in the ninth layer 819, through vias in the fourth through eighth layers 814–818, and into the large reagent/solvent channel 891 defined in the third layer 813. The liquid then flows to the large forked channel 892 in the fourth layer 814, through the two smaller forked channels 893A–893B in the fifth layer 815, through the porous material 877A, into six reagent/solvent channel segments 894A–894N in the fourth layer 814, through the porous material 877B, into six reagent/solvent channel segments 895A–895N in the fifth layer 815, through the porous material 877C, into six reagent/solvent channel segments 896A–896N in the fourth layer 814, through the porous element 877D, and into six reagent/solvent channel segments 897A–897N in the fifth layer 815. The solvent then flows through the porous material 877N, through vias 847A–847N in the fourth layer 814, through the vias 848A–848N in the third layer 813 and into the sample/reagent loading channels 850A–850N defined in the second layer 812. While the porous element 877A–877N technically do not retain any solid material within the device 810, they may be fabricated from the same material as the sample/reagent loading porous element 859, the outlet porous element 831 and the solvent waste porous element 884, which do retain solid material within the fluid process regions 828A–828N. The purpose of the porous elements 877A–877N is to elevate the effective fluidic impedance to each fluid process region, so that the fluidic impedance among fluid process regions containing different particle types will be more even, thus ensuring a smaller variation in common fluid flow rates between the fluid process regions with different types of solid materials. The reagent/solvent that flows into the sample/reagent loading channels 850A–850N defined in the second layer 812 then carries the samples/reagents into the narrow loading channels 854A–854N defined in the third layer 813, through vias 856A–856N defined in the fourth and fifth layers 814, 815, through the sample/reagent loading porous element 859, through vias 860A–860N defined in the sixth layer 816 and onto each of the six fluid process channels 828A–828N defined in the seventh layer 817.

To prepare the device 810 for operation, common reagent/solvent may be supplied to the device 810 through the reagent/solvent inlet port 890 defined in the ninth layer 819. These reagents/solvents may include multiple liquids that are pre-mixed upstream of the device 810 using a conventional micromixer. This common reagent/solvent distribution network is also used to supply the common reagent/solvent for the fluid process, once the samples/reagents (preferably different for each fluid process region) are loaded onto the fluid process regions. To prepare the device 810 for sample/reagent loading, the common reagent/solvent flow is temporarily interrupted, an external interface (not shown) previously covering the multiple sample/reagent loading ports 852A–852N is opened, and samples/reagents are supplied through the sample/reagent ports 852A–852N into the sample/reagent loading channels 850A–850N. The porous elements 877A–877N and the porous element 859 provide substantial fluidic impedance that prevents fluid flow through the porous elements 877A–877N, 859 at low pressures. This ensures that the samples/reagents remain isolated within the sample/reagent loading channels 850A–850N during the sample/reagent loading procedure. Following sample/reagent loading, the sample/reagent loading ports 852A–852N are again sealed (e.g., with an external interface) and common reagent/solvent flow is re-initiated to carry the samples/reagents into the fluid process regions 828A–828N defined in the seventh layer 817.

While the bulk of the reagent/solvent that is supplied to each fluid process channel 828A–828N travels downstream through the fluid process channels 828A–828N, a small split portion of each travels upstream through the fluid process channels 828A–828N in the direction of the waste port 886. The split portions of reagent/solvent from each fluid process region 828A–828N that travel upstream are consolidated into a single waste stream that flows through the slurry distribution network comprising the two small forked channels 826A and 826B, slurry channels 823A and 823B, then through vias 834A and 834B, the short waste segments 836A and 836B, vias 838A and 838B, vias 839A and 839B, porous element 884, vias 840A and 840B, a waste channel 882, to the waste port 886 to exit the device 810. The purpose of providing both an upstream and downstream path for each fluid process channel 828A–828N is to allow the removal of air bubbles from the device 810 during device preparation.

FIG. 18E shows the top view of the assembled device 810. FIG. 18F shows the slurry distribution network 810D (comprising various elements depicted in any of the preceding FIGS. 18A–18C, including slurry channels 823A–823B, solvent waste channel segments 836A–836B, solvent waste channel 882, two small forked channels 826A and 826B, six separation channels 828A–828N and six fluid process channel outlet vias 830A–830N). FIG. 18G shows the common reagent/solvent distribution network 810E (comprising various elements depicted in any of the preceding FIGS. 18A–18C, including channel segment 891, large forked channel 892, two small forked channels 893A and 893B, six reagent/solvent channel segments 894A–894N, six reagent/solvent channel segments 895A–895N, six reagent/solvent channel segments 896A–896N, and six reagent/solvent channel segments 897A–897N).

Depending on whether the solid material comprises catalyst material or stationary phase material, the device 810 may be used to perform parallel synthesis or analysis. In one example, the device 810 may be used as a flow-through chemical synthesis system that contains two different types of catalyst materials. The entire device 810 may be heated during operation in order to optimize the reactions conducted therein. Such heating may be performed with an external (e.g., conductive, convective, or radiative) heat source (not shown), or by heating elements, such as resistive electrodes (not shown), disposed within the device 810 and connected to an external power source (not shown). The reaction products may be collected at the outlets 832A–832N and analyzed by any of various techniques to monitor the reaction progress. Alternatively, a flow-through detection system can be used to monitor the reaction progress. In the device 810, each fluid process channel 828A–828N may have variable conditions that must be calibrated in order to fully understand how the various catalysts are affecting the overall synthetic strategy.

In one embodiment, the device 810 may be used to study the how each of the various catalysts affect the kinetics and/or yield of a reaction of interest, for example A+B→C. However, there may exist uneven or differential heating within the device 810 such that the temperature in each of the column areas may not be identical. Since most synthetic chemical reactions are variable with temperature, it may be necessary to calibrate the temperature of each fluid process channel 828A–828N prior to the introduction of the reactants of interest. In one preferred embodiment, a first synthetic reaction (for instance D+E→F) that is completely independent of the amount or type of solid catalyst material is performed in each of the fluid process regions 828A–828N as a calibration run. Common reactants D and E may be either pre-mixed or mixed in the fluid process regions 828A–828N as they are evenly distributed throughout the fluid process regions 828A–828N. The resulting solution is monitored at external detection regions (for instance, with a UV absorption wavelength that is only substantive when the product F is present) or the solution may be collected board for subsequent analysis (e.g., with mass spectrometry or nuclear magnetic resonance). In one embodiment, the relative temperature in each of the reaction chambers can be determine using the Gibbs free energy equation:

$$\Delta G = \frac{-RT}{\ln K_{eq}}$$

ΔG for the reaction in each fluid process region will be the same, but the equilibrium constants for the reaction going to partial completion will be related to the temperatures. Thus, the ratio of reactants to products may be monitored in each fluid process region, and the relative (and absolute) temperatures within that each fluid process region may be calculated to derive correction factors. Then, these temperature values may be used when the unknown reactants are actually used and the catalyst material affects the total kinetics and equilibrium.

In another embodiment, the temperature within the device 810 is known and constant. However, catalyst resins of different sizes are used in the two groups of fluid process regions (e.g., group 828A–828C and group 828D–828N) are used. Alternatively, the same size catalyst may be used but the reaction area volume and/or length may be varied. In order to determine the relative volume and/or catalyst surface area within a region, a first (calibration) reaction wherein the catalyst-dependent reaction effects are well understood may be conducted to determine correction factors. Then, one or more factors taking into account the total surface area of the catalyst for a particular fluid process region are generated and then applied to all subsequent unknown analysis in that fluid process region.

Although embodiments of the present invention has been described in detail by way of illustration and example to promote clarity and understanding, it will be apparent that certain changes and modifications may be practiced within the scope of the appended claims.

What is claimed is:

1. A multi-column liquid chromatography data correction methods comprising the steps of:

providing a plurality of liquid chromatography columns in fluid communication with a common mobile phase source, each column of the plurality of columns containing a stationary phase material, wherein the mobile phase source supplies a mobile phase to the plurality of columns at a selected mobile phase source output flow rate;

providing at least one detector in sensory communication with the plurality of columns;

supplying a calibrant having at least a first component to each column of the plurality of columns;

eluting the at least a first component of the calibrant in each column of the plurality columns according to a first mobile phase source output flow rate and a first mobile phase composition profile;

measuring, for each column of the plurality of columns, a first physical parameter using the at least one detector;

deriving, for each column of the plurality of columns, at least one correction factor based on the first physical parameter;

supplying, to each column of the plurality of columns, at least one sample containing a plurality of sample components;

eluting at least two components of the plurality of sample components of the at least one sample in each column of the plurality of columns to obtain raw chromatographic data; and applying, for each column of the plurality of columns, the at least one correction factor to the raw chromatographic data to yield corrected chromatographic output data.

2. The method of claim 1 wherein the corrected chromatographic output data includes any of: corrected retention times, corrected peak areas, corrected baselines, corrected mass throughput, and corrected multiple wavelength correction.

3. The method of claim 1 wherein the at least a first component of the calibrant includes two components having different retention characteristics relative to the stationary phase material.

4. The method of claim 1 wherein the sample elution step is performed according to the first mobile phase source output flow rate and the first mobile phase composition profile.

5. The method of claim 1 wherein the measuring step is performed inferentially.

6. The method of claim 1 wherein the measuring step is performed substantially downstream of each column of the plurality of columns.

7. The method of claim 1 wherein the first physical parameter comprises any of absorbance, fluorescence, optical scattering, evaporative light scattering, temperature profile, voltage profile, current profile, molecular weight, molecular composition, elemental composition, flow, and pressure.

8. The method of claim 1, further comprising the step of recording, for each column of the plurality of columns, the first physical parameter as a function of time.

9. The method of claim 1 wherein the mobile phase comprises a first mobile phase fluid and a second mobile phase fluid, the method further comprising the step of mixing the first mobile phase fluid and the second mobile phase fluid, wherein the composition of the mobile phase changes during each of the calibrant elution step and the sample elution step.

10. The method of claim 1, further comprising the step of flushing the plurality of columns between the calibrant elution step and the sample elution step.

11. The method of claim 1 wherein the common mobile phase source comprises a plurality of pumps and a plurality of fluid reservoirs.

12. The method of claim 1 wherein the sample supplying step includes supplying a different sample of the at least one sample to each column of the plurality of columns.

13. The method of claim 1 wherein each column of the plurality of columns is microfluidic.

14. The method of claim 1 wherein the at least one detector includes a plurality of detector channels, wherein each detector channel of the plurality of detector channels is in indirect sensory communication with a different fluid process region of the plurality of fluid process regions.

15. The method of claim 1 wherein each column of the plurality of columns contains stationary phase material of substantially the same composition.

16. A method for correcting retention times in multi-column liquid chromatography, the method comprising the steps of:

providing a plurality of liquid chromatography columns in fluid communication with a common mobile phase source, each column of the plurality of columns containing a stationary phase material and having an associated detection region, wherein the mobile phase source supplies a mobile phase to the plurality of columns at a selected mobile phase source output flow rate;

providing, for the detection region associated with each column of the plurality of columns, a detector in sensory communication with the detection region;

supplying a first calibrant to each column of the plurality of columns, wherein the first calibrant contains at least a first component and a second component, with each of the first component and second component having different retention characteristics relative to the stationary phase material;

eluting the at least first component and second component in each column of the plurality of columns according to a first mobile phase source output flow rate and a first mobile phase composition profile;

measuring, for each column of the plurality of columns, a first time for the first component to reach the associated detection region and a second time for the second component to reach the associated detection region;

deriving, for each column of the plurality of columns, at least one correction factor based on at least one of the first time and the second time;

supplying, to each column of the plurality of columns, at least one sample containing a plurality of sample components;

eluting at least two components of the plurality of sample components of the sample in each column of the plurality of columns to obtain raw chromatographic data; and applying, for each column of the plurality of columns, the at least one correction factor to the raw chromatographic data to yield corrected chromatographic data with corrected retention times.

17. The method of claim 16, further comprising the step of cleaning the plurality of columns between the first elution step and the second elution step.

18. The method of claim 17 wherein the cleaning step includes maintaining a first mobile phase composition profile of at least seventy percent organic solvent.

19. The method of claim 16 wherein each column of the plurality of liquid chromatography columns is microfluidic.

20. The method of claim 19 wherein each column of the plurality of liquid chromatography columns is integrated into a single microfluidic device.

21. The method of claim 16 wherein the stationary phase material includes packed particulate matter.

22. The method of claim 16 wherein the mobile phase includes a first solvent, and the first mobile phase composition profile includes a substantially constant concentration of the first solvent.

23. The method of claim 16 wherein the mobile phase includes a plurality of solvents, and the mobile phase composition profile includes a variation in the weight percent of at least one solvent.

24. The method of claim 23, further comprising the step of mixing the plurality of solvents.

25. The method of claim 16 wherein the mobile phase includes a solute, and the mobile phase composition profile includes a variation in solute concentration.

26. The method of claim 16 wherein the mobile phase source includes at least one pump.

27. The method of claim 16 wherein the mobile phase source includes at least two fluid reservoirs.

28. The method of claim 16 wherein the elution of the at least two components of the plurality of sample components of the sample is performed according to the first mobile phase source output flow rate and the first mobile phase composition profile.

29. The method of claim 16 wherein the step of supplying at least one sample includes supplying a different sample to each column of the plurality of columns.

30. The method of claim 16 wherein the step of supplying at least one sample includes supplying substantially the same sample to at least two columns of the plurality of columns.

31. The method of claim 16 wherein the deriving step utilizes a least square fit method.

32. The method of claim 16 wherein any of the measuring, deriving, and applying steps are automated.

33. A multi-column chromatography system for performing the method of claim 16.

34. A system for correcting retention times in multi-column liquid chromatography, the system comprising:
- a plurality of liquid chromatography columns for performing pressure-driven chromatographic separations;
- a common mobile phase source in fluid communication with the plurality of columns;
- a plurality of detection regions associated with the plurality of separation columns;
- at least one detector in sensory communication with the plurality of detection regions;
- a data storage device for receiving and storing data obtained from the at least one detector; and
- a microprocessor for executing instructions to derive correction factors based on data obtained from the at least one detector, and to apply the correction factors to generate corrected chromatographic data with corrected retention times.

35. The system of claim 34 wherein the data storage device is integrated with the microprocessor.

36. The system of claim 34 wherein each column of the plurality of liquid chromatography columns is microfluidic.

37. The system of claim 34 wherein the plurality of chromatography columns is integrated within a substantially planar microfluidic device.

38. The system of claim 37 wherein the plurality of detection regions comprises a plurality of substantially optically transmissive regions within the microfluidic device.

39. The system of claim 37 wherein the plurality of detection regions is disposed within a multi-channel flow cell.

40. The system of claim 34 wherein the common mobile phase source includes a plurality of pumps.

41. The system of claim 34, further comprising a degasser in fluid communication with the common mobile phase source.

42. The system of claim 40, further comprising a mixer disposed between the plurality of pumps and the plurality of liquid chromatography columns.

43. The system of claim 34 wherein the detector comprises an electromagnetic source and electromagnetic receiver.

44. The system of claim 34 wherein the detector comprises a plurality of fiber optic conduits.

* * * * *

UNITED STATES PATENT AND TRADEMARK OFFICE
CERTIFICATE OF CORRECTION

| | |
|---|---|
| PATENT NO. | : 7,178,386 B1 |
| APPLICATION NO. | : 10/821567 |
| DATED | : February 20, 2007 |
| INVENTOR(S) | : Ronald C. Gamble et al. |

It is certified that error appears in the above-identified patent and that said Letters Patent is hereby corrected as shown below:

In column 2, line 48, "may be Separated" should be -- may be separated --.

In column 15, line 27, "relative to the Separation" should be -- relative to the separation --.

In column 22, lines 19-20, "degree of porosity Of" should be -- degree of porosity of --.

Signed and Sealed this

Twenty-ninth Day of May, 2007

JON W. DUDAS
*Director of the United States Patent and Trademark Office*